(12) United States Patent
de Juan, Jr. et al.

(10) Patent No.: US 12,226,525 B2
(45) Date of Patent: **\*Feb. 18, 2025**

(54) NASOLACRIMAL DRAINAGE SYSTEM IMPLANTS FOR DRUG THERAPY

(71) Applicant: Mati Therapeutics, Inc.

(72) Inventors: Eugene de Juan, Jr., San Francisco, CA (US); Stephen Boyd, Murrieta, CA (US); Cary J. Reich, Los Gatos, CA (US); Alan R. Rapacki, Redwood City, CA (US); Hanson S. Gifford, Woodside, CA (US); Mark Deem, Mountain View, CA (US)

(73) Assignee: Mati Therapeutics, Inc.

( * ) Notice: Subject to any disclaimer, the term of this patent is extended or adjusted under 35 U.S.C. 154(b) by 578 days.

This patent is subject to a terminal disclaimer.

(21) Appl. No.: 17/133,980

(22) Filed: Dec. 24, 2020

(65) Prior Publication Data
US 2021/0212941 A1 Jul. 15, 2021

Related U.S. Application Data

(63) Continuation of application No. 16/544,884, filed on Aug. 19, 2019, now Pat. No. 10,874,606, which is a
(Continued)

(51) Int. Cl.
*A61K 9/00* (2006.01)
*A61F 9/00* (2006.01)
(Continued)

(52) U.S. Cl.
CPC .......... *A61K 9/0051* (2013.01); *A61F 9/0017* (2013.01); *A61F 9/0026* (2013.01);
(Continued)

(58) Field of Classification Search
CPC ...... A61K 9/0051; A61K 9/06; A61K 31/215; A61K 31/16; A61K 47/34
See application file for complete search history.

(56) References Cited

U.S. PATENT DOCUMENTS 2,962,023 A 11/1960 Gaston et al.
3,416,530 A 12/1968 Ness
(Continued)

FOREIGN PATENT DOCUMENTS

AU 20023644336 7/2003
EP 0442745 A1 8/1991
(Continued)

OTHER PUBLICATIONS

"U.S. Appl. No. 10/825,047, Preliminary Amendment and Response filed Aug. 18, 2008 toRestriction Requirement mailed Jul. 17, 2008", 10 pgs.
(Continued)

*Primary Examiner* — Carlos A Azpuru
(74) *Attorney, Agent, or Firm* — Koren Anderson

(57) ABSTRACT

An implant for insertion through a punctum and into a canalicular lumen of a patient. The implant includes a matrix of material, a therapeutic agent dispersed in the matrix of material, a sheath disposed over a portion of the matrix of material and configured to inhibit the therapeutic agent from being released from the matrix of material into the canalicular lumen and to allow the therapeutic agent to be released from a surface of the matrix of material to a tear film, and a retention structure configured to retain the implant within the canalicular lumen.

14 Claims, 30 Drawing Sheets

Related U.S. Application Data continuation of application No. 16/168,554, filed on Oct. 23, 2018, now Pat. No. 10,300,014, which is a continuation of application No. 15/852,619, filed on Dec. 22, 2017, now Pat. No. 10,383,817, which is a continuation of application No. 15/405,991, filed on Jan. 13, 2017, now Pat. No. 9,849,082, which is a continuation of application No. 14/858,555, filed on Sep. 18, 2015, now Pat. No. 9,549,852, which is a continuation of application No. 14/265,071, filed on Apr. 29, 2014, now Pat. No. 9,168,222, which is a continuation of application No. 13/184,690, filed on Jul. 18, 2011, now Pat. No. 8,747,884, which is a continuation of application No. 11/695,545, filed on Apr. 2, 2007, now Pat. No. 7,998,497.

(60) Provisional application No. 60/871,864, filed on Dec. 26, 2006, provisional application No. 60/787,775, filed on Mar. 31, 2006.

(51) Int. Cl.

| | |
|---|---|
| *A61F 9/007* | (2006.01) |
| *A61K 9/06* | (2006.01) |
| *A61K 31/215* | (2006.01) |
| *A61K 31/216* | (2006.01) |
| *A61K 31/55* | (2006.01) |
| *A61K 31/557* | (2006.01) |
| *A61K 31/5575* | (2006.01) |
| *A61K 31/573* | (2006.01) |
| *A61K 47/34* | (2017.01) |
| *A61L 31/16* | (2006.01) |

(52) U.S. Cl.
CPC ...... *A61F 9/00772* (2013.01); *A61F 9/00781* (2013.01); *A61K 9/00* (2013.01); *A61K 9/0017* (2013.01); *A61K 9/06* (2013.01); *A61K 31/215* (2013.01); *A61K 31/216* (2013.01); *A61K 31/55* (2013.01); *A61K 31/557* (2013.01); *A61K 31/5575* (2013.01); *A61K 31/573* (2013.01); *A61K 47/34* (2013.01); *A61L 31/16* (2013.01); *A61F 2220/0008* (2013.01); *A61F 2250/0067* (2013.01); *A61F 2250/0087* (2013.01)

(56) References Cited

U.S. PATENT DOCUMENTS

| | | |
|---|---|---|
| 3,618,604 A | 11/1971 | Ness |
| 3,626,940 A | 12/1971 | Zaffaroni |
| 3,710,795 A | 1/1973 | Higuchi et al. |
| 3,826,258 A | 7/1974 | Abraham |
| 3,828,777 A | 8/1974 | Ness |
| 3,832,252 A | 8/1974 | Higuchi et al. |
| 3,845,201 A | 10/1974 | Haddad et al. |
| 3,845,770 A | 11/1974 | Theeuwes et al. |
| 3,865,108 A | 2/1975 | Hartop |
| 3,880,991 A | 4/1975 | Yolles |
| 3,949,750 A | 4/1976 | Freeman |
| 3,960,150 A | 6/1976 | Hussain et al. |
| 3,962,414 A | 6/1976 | Michaels |
| 3,993,071 A | 11/1976 | Higuchi et al. |
| 4,014,335 A | 3/1977 | Arnold |
| 4,052,505 A | 10/1977 | Higuchi et al. |
| 4,121,648 A | 10/1978 | Medovar et al. |
| 4,142,526 A | 3/1979 | Zaffaroni et al. |
| 4,164,559 A | 8/1979 | Miyata et al. |
| 4,249,531 A | 2/1981 | Heller et al. |
| 4,281,654 A | 8/1981 | Shell et al. |
| 4,304,765 A | 12/1981 | Shell et al. |
| 4,322,323 A | 3/1982 | Capozza |
| 4,521,210 A | 6/1985 | Wong |
| 4,540,408 A | 9/1985 | Lloyd |
| 4,660,546 A | 4/1987 | Herrick et al. |
| 4,747,404 A | 5/1988 | Jampel et al. |
| 4,851,228 A | 7/1989 | Zentner et al. |
| 4,853,224 A | 8/1989 | Wong |
| 4,886,488 A | 12/1989 | White |
| 4,915,684 A | 4/1990 | MacKeen et al. |
| 4,938,763 A | 7/1990 | Dunn et al. |
| 4,959,048 A | 9/1990 | Seder et al. |
| 4,997,652 A | 3/1991 | Wong |
| 5,041,081 A | 8/1991 | Odrich |
| 5,049,142 A | 9/1991 | Herrick et al. |
| 5,053,030 A | 10/1991 | Herrick et al. |
| 5,077,033 A | 12/1991 | Viegas et al. |
| 5,077,049 A | 12/1991 | Dunn et al. |
| 5,098,443 A | 3/1992 | Parel et al. |
| 5,116,371 A | 5/1992 | Christensen et al. |
| 5,128,058 A | 7/1992 | Ishii et al. |
| 5,133,159 A | 7/1992 | Nelson |
| 5,143,724 A | 9/1992 | Leshchiner et al. |
| 5,163,959 A | 11/1992 | Herrick |
| 5,164,188 A | 11/1992 | Wong |
| 5,171,270 A | 12/1992 | Herrick |
| 5,254,089 A | 10/1993 | Wang |
| 5,278,202 A | 1/1994 | Dunn et al. |
| 5,283,063 A | 2/1994 | Freeman |
| 5,300,114 A | 4/1994 | Gwon et al. |
| 5,304,121 A | 4/1994 | Sahatjian |
| 5,318,513 A | 6/1994 | Leib et al. |
| 5,322,691 A | 6/1994 | Darougar et al. |
| 5,324,519 A | 6/1994 | Dunn et al. |
| 5,334,137 A | 8/1994 | Freeman |
| 5,378,475 A | 1/1995 | Smith et al. |
| 5,395,618 A | 3/1995 | Darougar et al. |
| 5,417,651 A | 5/1995 | Guena et al. |
| 5,423,777 A | 6/1995 | Tajiri et al. |
| 5,443,505 A | 8/1995 | Wong et al. |
| 5,466,233 A | 11/1995 | Weiner et al. |
| 5,476,511 A | 12/1995 | Gwon et al. |
| 5,501,856 A | 3/1996 | Ohtori et al. |
| 5,514,379 A | 5/1996 | Weissleder et al. |
| 5,545,208 A | 8/1996 | Wolff et al. |
| 5,556,633 A | 9/1996 | Haddad et al. |
| 5,575,815 A | 11/1996 | Slepian et al. |
| 5,624,975 A | 4/1997 | Valencia |
| 5,634,946 A | 6/1997 | Slepian |
| 5,707,643 A | 1/1998 | Ogura et al. |
| 5,714,360 A | 2/1998 | Swan et al. |
| 5,723,005 A | 3/1998 | Herrick |
| 5,741,292 A | 4/1998 | Mendius |
| 5,741,551 A | 4/1998 | Guire et al. |
| 5,766,242 A | 6/1998 | Wong et al. |
| 5,766,243 A | 6/1998 | Christensen et al. |
| 5,770,589 A | 6/1998 | Billson et al. |
| 5,773,019 A | 6/1998 | Ashton et al. |
| 5,780,044 A | 7/1998 | Yewey et al. |
| 5,824,048 A | 10/1998 | Tuch |
| 5,824,072 A | 10/1998 | Wong |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,843,156 A | 12/1998 | Slepian et al. |
| 5,858,653 A | 1/1999 | Duran et al. |
| 5,869,079 A | 2/1999 | Wong et al. |
| 5,871,535 A | 2/1999 | Wolff et al. |
| 5,879,697 A | 3/1999 | Ding et al. |
| 5,902,598 A | 5/1999 | Chen et al. |
| 5,928,662 A | 7/1999 | Phillips |
| 5,947,974 A | 9/1999 | Brady et al. |
| 5,961,370 A | 10/1999 | Valle et al. |
| 5,962,383 A | 10/1999 | Doyel et al. |
| 5,993,407 A | 11/1999 | Moazed |
| 6,001,386 A | 12/1999 | Ashton et al. |
| 6,004,346 A | 12/1999 | Wolff et al. |
| 6,010,391 A | 1/2000 | Lewellen et al. |
| 6,015,433 A | 1/2000 | Roth |
| 6,016,806 A | 1/2000 | Webb |

(56) References Cited

U.S. PATENT DOCUMENTS

| | | | |
|---|---|---|---|
| 6,027,245 A | 2/2000 | Houser et al. | |
| 6,027,470 A | 2/2000 | Mendius | |
| 6,041,785 A | 3/2000 | Webb | |
| 6,042,875 A | 3/2000 | Ding et al. | |
| 6,054,485 A | 4/2000 | Schwartz et al. | |
| 6,074,661 A | 6/2000 | Olejnik et al. | |
| 6,077,698 A | 6/2000 | Swan et al. | |
| 6,082,362 A | 7/2000 | Webb | |
| 6,095,901 A | 8/2000 | Robinson et al. | |
| 6,110,483 A | 8/2000 | Whitbourne et al. | |
| 6,117,441 A | 9/2000 | Moo-Young et al. | |
| 6,117,907 A | 9/2000 | Sher | |
| 6,149,684 A | 11/2000 | Herrick | |
| 6,196,993 B1 | 3/2001 | Cohan et al. | |
| 6,214,901 B1 | 4/2001 | Chudzik et al. | |
| 6,217,895 B1 | 4/2001 | Guo et al. | |
| 6,224,630 B1 | 5/2001 | Bao et al. | |
| 6,225,348 B1 | 5/2001 | Paulsen | |
| 6,234,175 B1 | 5/2001 | Zhou et al. | |
| 6,238,363 B1 | 5/2001 | Kurihashi | |
| 6,254,562 B1 | 7/2001 | Fouere | |
| 6,264,971 B1 | 7/2001 | Darougar et al. | |
| 6,278,018 B1 | 8/2001 | Swan | |
| 6,290,684 B1 | 9/2001 | Herrick | |
| 6,306,114 B1 | 10/2001 | Freeman et al. | |
| 6,331,313 B1 | 12/2001 | Wong et al. | |
| 6,344,047 B1 | 2/2002 | Price et al. | |
| 6,350,781 B1 | 2/2002 | Shahinia | |
| 6,368,615 B1 | 4/2002 | Guttag | |
| 6,369,116 B1 | 4/2002 | Wong et al. | |
| 6,371,122 B1 | 4/2002 | Mandelkorn | |
| 6,375,972 B1 | 4/2002 | Guo et al. | |
| 6,383,192 B1 | 5/2002 | Kurihashi | |
| 6,416,777 B1 | 7/2002 | Yaacobi | |
| 6,416,780 B1 | 7/2002 | Passmore et al. | |
| 6,428,502 B1 | 8/2002 | Lang | |
| 6,441,047 B2 | 8/2002 | DeSantis | |
| 6,455,062 B1 | 9/2002 | Olejnik et al. | |
| 6,512,747 B1 | 1/2003 | Umeuchi et al. | |
| 6,534,693 B2 | 3/2003 | Fischell et al. | |
| 6,548,078 B2 | 4/2003 | Guo et al. | |
| 6,605,108 B2 | 8/2003 | Mendius et al. | |
| 6,629,533 B1 | 10/2003 | Webb et al. | |
| 6,645,963 B2 | 11/2003 | Higashiyama et al. | |
| 6,699,493 B2 | 3/2004 | Wong | |
| 6,706,034 B1 | 3/2004 | Bhat | |
| 6,706,275 B1 | 3/2004 | Camp | |
| 6,713,081 B2 | 3/2004 | Robinson et al. | |
| 6,729,939 B2 | 5/2004 | Wrue | |
| 6,743,439 B1 | 6/2004 | Castillo et al. | |
| 6,756,049 B2 | 6/2004 | Brubaker et al. | |
| 6,780,164 B2 | 8/2004 | Bergheim et al. | |
| 6,840,931 B2 | 1/2005 | Peterson et al. | |
| 6,846,318 B2 | 1/2005 | Camp | |
| 6,866,563 B2 | 3/2005 | Green | |
| 6,964,781 B2 | 11/2005 | Brubaker | |
| 6,982,090 B2 | 1/2006 | Gillespie | |
| 6,991,808 B2 | 1/2006 | Brubaker et al. | |
| 6,994,684 B2 | 2/2006 | Murray et al. | |
| 7,001,615 B1 | 2/2006 | Singh et al. | |
| 7,008,667 B2 | 3/2006 | Chudzik et al. | |
| 7,017,580 B2 | 3/2006 | Prescott et al. | |
| 7,117,870 B2 | 10/2006 | Prescott | |
| 7,135,009 B2 | 11/2006 | Tu et al. | |
| 7,204,253 B2 | 4/2007 | Mendius et al. | |
| 7,204,995 B2 | 4/2007 | El-Sherif et al. | |
| 7,510,541 B2 | 3/2009 | Hanna | |
| 7,662,864 B2 | 2/2010 | Kanamathareddy et al. | |
| 7,752,519 B2 | 7/2010 | Yeo et al. | |
| 7,986,633 B2 | 7/2011 | Ryu et al. | |
| 7,998,497 B2 * | 8/2011 | de Juan, Jr. | A61K 31/5575 424/423 |
| 8,691,265 B2 | 4/2014 | Juan et al. | |
| 8,747,884 B2 * | 6/2014 | De Juan, Jr. | A61K 31/216 424/425 |
| 8,795,711 B2 * | 8/2014 | de Juan, Jr. | A61K 31/5575 604/294 |
| 9,168,222 B2 * | 10/2015 | De Juan, Jr. | A61P 43/00 |
| 9,549,852 B2 | 1/2017 | Juan, Jr. et al. | |
| 9,849,082 B2 | 12/2017 | Juan et al. | |
| 10,300,014 B2 * | 5/2019 | de Juan, Jr. | A61P 9/00 |
| 10,383,817 B2 * | 8/2019 | de Juan, Jr. | A61L 31/16 |
| 10,874,606 B2 * | 12/2020 | de Juan, Jr. | A61F 9/00772 |
| 2002/0028181 A1 | 3/2002 | Miller et al. | |
| 2002/0032298 A1 | 3/2002 | Bennett et al. | |
| 2002/0032400 A1 | 3/2002 | Moazed | |
| 2002/0055701 A1 | 5/2002 | Fischell et al. | |
| 2002/0103255 A1 | 8/2002 | Hellberg et al. | |
| 2002/0111576 A1 | 8/2002 | Greene et al. | |
| 2002/0138154 A1 | 9/2002 | Li et al. | |
| 2002/0151960 A1 | 10/2002 | Mendius et al. | |
| 2002/0193441 A1 | 12/2002 | Robertson | |
| 2002/0198453 A1 | 12/2002 | Herrick | |
| 2003/0095534 A1 | 5/2003 | Jiang | |
| 2003/0096831 A1 | 5/2003 | Stone et al. | |
| 2003/0097151 A1 | 5/2003 | Smedley et al. | |
| 2003/0130612 A1 | 7/2003 | Moazed | |
| 2003/0143280 A1 | 7/2003 | El-Sherif et al. | |
| 2003/0149479 A1 | 8/2003 | Snyder et al. | |
| 2003/0152522 A1 | 8/2003 | Miller et al. | |
| 2003/0175324 A1 | 9/2003 | Robinson et al. | |
| 2003/0176854 A1 | 9/2003 | Rodstrom | |
| 2004/0009222 A1 | 1/2004 | Chou et al. | |
| 2004/0020253 A1 | 2/2004 | Hurskainen et al. | |
| 2004/0043067 A1 | 3/2004 | Salamone et al. | |
| 2004/0071761 A1 | 4/2004 | Miller et al. | |
| 2004/0081081 A1 | 4/2004 | Colombo | |
| 2004/0092435 A1 | 5/2004 | Peyman | |
| 2004/0100929 A1 | 5/2004 | Garcia-Luna-Aceves | |
| 2004/0102729 A1 | 5/2004 | Haffner et al. | |
| 2004/0116524 A1 | 6/2004 | Cohen et al. | |
| 2004/0121014 A1 | 6/2004 | Guo et al. | |
| 2004/0127843 A1 | 7/2004 | Tu et al. | |
| 2004/0137068 A1 | 7/2004 | Bhushan | |
| 2004/0141151 A1 | 7/2004 | Gillespie | |
| 2004/0144392 A1 | 7/2004 | Mueller | |
| 2004/0147870 A1 | 7/2004 | Burns et al. | |
| 2004/0156345 A1 | 8/2004 | Steer et al. | |
| 2004/0170685 A1 | 9/2004 | Carpenter et al. | |
| 2004/0175410 A1 | 9/2004 | Ashton et al. | |
| 2004/0176341 A1 | 9/2004 | Chou et al. | |
| 2004/0176749 A1 | 9/2004 | Lohmann et al. | |
| 2004/0180075 A1 | 9/2004 | Robinson et al. | |
| 2004/0185887 A1 | 9/2004 | Wolman et al. | |
| 2004/0193095 A1 | 9/2004 | Shadduck | |
| 2004/0208910 A1 | 10/2004 | Ashton et al. | |
| 2004/0210182 A1 | 10/2004 | Fouere et al. | |
| 2004/0236343 A1 | 11/2004 | Taylor et al. | |
| 2004/0249333 A1 | 12/2004 | Bergheim et al. | |
| 2004/0254516 A1 | 12/2004 | Murray et al. | |
| 2004/0265356 A1 | 12/2004 | Mosack | |
| 2005/0008673 A1 | 1/2005 | Snyder et al. | |
| 2005/0043412 A1 | 2/2005 | Ichikawa et al. | |
| 2005/0048121 A1 | 3/2005 | East et al. | |
| 2005/0054723 A1 | 3/2005 | Stjernschantz | |
| 2005/0055078 A1 | 3/2005 | Campbell | |
| 2005/0064010 A1 | 3/2005 | Cooper et al. | |
| 2005/0095269 A1 | 5/2005 | Ainpour et al. | |
| 2005/0107734 A1 | 5/2005 | Coroneo | |
| 2005/0112175 A1 | 5/2005 | Yaacobi | |
| 2005/0119737 A1 | 6/2005 | Bene et al. | |
| 2005/0129731 A1 | 6/2005 | Horres et al. | |
| 2005/0192527 A1 | 9/2005 | Gharib et al. | |
| 2005/0197614 A1 * | 9/2005 | Pritchard | A61F 9/00772 604/8 |
| 2005/0220882 A1 | 10/2005 | Pritchard et al. | |
| 2005/0228477 A1 | 10/2005 | Grainger et al. | |
| 2005/0232972 A1 | 10/2005 | Odrich | |
| 2005/0244461 A1 | 11/2005 | Nivaggioli et al. | |
| 2005/0244464 A1 | 11/2005 | Hughes | |
| 2005/0244469 A1 | 11/2005 | Whitcup et al. | |
| 2005/0244506 A1 | 11/2005 | Burke et al. | |
| 2005/0255144 A1 | 11/2005 | Schultz | |
| 2005/0255564 A1 | 11/2005 | Sakai et al. | |

(56) References Cited

U.S. PATENT DOCUMENTS

| | | |
|---|---|---|
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0030669 A1 | 2/2006 | Taton et al. |
| 2006/0074370 A1 | 4/2006 | Zhou |
| 2006/0100700 A1 | 5/2006 | Bernard et al. |
| 2006/0106352 A1 | 5/2006 | Kurihashi |
| 2006/0110429 A1 | 5/2006 | Reiff et al. |
| 2006/0122553 A1 | 6/2006 | Hanna |
| 2006/0171985 A1 | 8/2006 | Richard et al. |
| 2006/0182783 A1 | 8/2006 | Hughes et al. |
| 2006/0188576 A1 | 8/2006 | Takruri |
| 2006/0292099 A1 | 12/2006 | Milburn et al. |
| 2007/0021762 A1 | 1/2007 | Liu et al. |
| 2007/0043332 A1 | 2/2007 | Malcolm et al. |
| 2007/0083146 A1 | 4/2007 | Murray |
| 2007/0088444 A1 | 4/2007 | Hodorek et al. |
| 2007/0123924 A1 | 5/2007 | Becker |
| 2007/0132125 A1 | 6/2007 | Rastogi et al. |
| 2007/0135914 A1 | 6/2007 | Herrick |
| 2007/0243230 A1 | 10/2007 | Juan et al. |
| 2007/0269487 A1 | 11/2007 | Juan et al. |
| 2007/0298075 A1 | 12/2007 | Borgia et al. |
| 2007/0299515 A1 | 12/2007 | Herrick |
| 2007/0299516 A1 | 12/2007 | Cui et al. |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2008/0181930 A1 | 7/2008 | Rodstrom et al. |
| 2008/0299176 A1 | 12/2008 | Lai et al. |
| 2009/0092654 A1 | 4/2009 | Juan, Jr. et al. |
| 2009/0099626 A1 | 4/2009 | Juan et al. |
| 2009/0104243 A1 | 4/2009 | Utkhede et al. |
| 2009/0104248 A1 | 4/2009 | Rapacki et al. |
| 2009/0105749 A1 | 4/2009 | Juan et al. |
| 2009/0118702 A1 | 5/2009 | Lazar |
| 2009/0122765 A1 | 5/2009 | Dimou et al. |
| 2009/0252236 A1 | 10/2009 | Li et al. |
| 2009/0264861 A1 | 10/2009 | Jain et al. |
| 2009/0280158 A1 | 11/2009 | Butuner |
| 2009/0298390 A1 | 12/2009 | Rapacki et al. |
| 2010/0034870 A1 | 2/2010 | Sim et al. |
| 2010/0040670 A1 | 2/2010 | Odrich et al. |
| 2010/0189766 A1 | 7/2010 | Utkhede et al. |
| 2010/0209477 A1 | 8/2010 | Butuner et al. |
| 2010/0274204 A1 | 10/2010 | Rapacki et al. |
| 2010/0274224 A1 | 10/2010 | Jain et al. |
| 2012/0318281 A1 | 12/2012 | Rapacki et al. |
| 2014/0161863 A1 | 6/2014 | Juan et al. |

FOREIGN PATENT DOCUMENTS

| | | | |
|---|---|---|---|
| EP | 0621022 A1 | 10/1994 | |
| EP | 0621022 B1 | 7/1999 | |
| EP | 0988844 A2 | 3/2000 | |
| EP | 0988844 A3 | 7/2001 | |
| EP | 2010096 A2 | 1/2009 | |
| EP | 2097044 A1 | 9/2009 | |
| GB | 2216795 A | 10/1989 | |
| JP | 7178130 A | 7/1995 | |
| JP | 10033584 | 2/1998 | |
| JP | 11505159 A | 5/1999 | |
| JP | 2004202276 A | 7/2004 | |
| JP | 2005000628 A | 1/2005 | |
| JP | 2005058622 A | 3/2005 | |
| JP | 2005110765 A | 4/2005 | |
| JP | 2005110930 A | 4/2005 | |
| JP | 2005512607 A | 5/2005 | |
| JP | 2005532103 A | 10/2005 | |
| JP | 2005312835 A | 11/2005 | |
| JP | 2005319190 A | 11/2005 | |
| JP | 2005328922 A | 12/2005 | |
| JP | 2006516619 A | 7/2006 | |
| JP | 2006524507 A | 11/2006 | |
| JP | 2007067910 A | 3/2007 | |
| JP | 2007178130 A | 7/2007 | |
| JP | 2007195819 A | 8/2007 | |
| JP | 2009503335 A | 1/2009 | |
| JP | 4339635 B2 | 10/2009 | |
| JP | 4346438 B2 | 10/2009 | |
| JP | 2011505159 A | 2/2011 | |
| JP | 2011507269 A | 3/2011 | |
| JP | 2011514898 A | 5/2011 | |
| JP | 2016213964 A | 12/2016 | |
| NZ | 581461 A | 4/2011 | |
| WO | 1993012765 A1 | 7/1993 | |
| WO | 9501764 A2 | 1/1995 | |
| WO | 1995001764 A2 | 1/1995 | |
| WO | 9528984 A1 | 11/1995 | |
| WO | 1995028984 A1 | 11/1995 | |
| WO | 9636377 A1 | 11/1996 | |
| WO | 9640005 A1 | 12/1996 | |
| WO | 9711655 A1 | 4/1997 | |
| WO | 1997011655 A1 | 4/1997 | |
| WO | 9720578 A1 | 6/1997 | |
| WO | 9833461 A1 | 8/1998 | |
| WO | 9842282 A1 | 10/1998 | |
| WO | 9937260 A1 | 7/1999 | |
| WO | 9944553 A1 | 9/1999 | |
| WO | 9964089 A1 | 12/1999 | |
| WO | 9965544 A1 | 12/1999 | |
| WO | 2000003705 A1 | 1/2000 | |
| WO | 2000027321 A1 | 5/2000 | |
| WO | 0062760 A1 | 10/2000 | |
| WO | 2001030323 A2 | 5/2001 | |
| WO | 0180825 A2 | 11/2001 | |
| WO | 0211783 A1 | 2/2002 | |
| WO | 02058667 A2 | 8/2002 | |
| WO | 2002080811 A2 | 10/2002 | |
| WO | 2002083198 A2 | 10/2002 | |
| WO | 2003009784 A1 | 2/2003 | |
| WO | 2003015667 A1 | 2/2003 | |
| WO | 03022242 A1 | 3/2003 | |
| WO | 2003017897 A2 | 3/2003 | |
| WO | 2003057101 A1 | 7/2003 | |
| WO | 2003061625 A2 | 7/2003 | |
| WO | 2004004614 A2 | 1/2004 | |
| WO | 2004024043 A2 | 3/2004 | |
| WO | 2004066979 A2 | 8/2004 | |
| WO | 2004066980 A2 | 8/2004 | |
| WO | 2004078140 A2 | 9/2004 | |
| WO | 2004105658 A1 | 12/2004 | |
| WO | 2004112639 A2 | 12/2004 | |
| WO | 2005000154 A2 | 1/2005 | |
| WO | 2005051234 A2 | 6/2005 | |
| WO | 2005060210 A1 | 6/2005 | |
| WO | 2005086694 A2 | 9/2005 | |
| WO | 2006002112 A1 | 1/2006 | |
| WO | 2006002366 A1 | 1/2006 | |
| WO | 2006014434 A2 | 2/2006 | |
| WO | 2006014793 A1 | 2/2006 | |
| WO | 2006031658 A2 | 3/2006 | |
| WO | 2006044669 A2 | 4/2006 | |
| WO | 2006057859 A1 | 6/2006 | |
| WO | 2006096586 A1 | 9/2006 | |
| WO | 2006122414 A1 | 11/2006 | |
| WO | 2007008262 A2 | 1/2007 | |
| WO | 2007115259 A2 | 10/2007 | |
| WO | 2007115261 A2 | 10/2007 | |
| WO | 2007149771 A2 | 12/2007 | |
| WO | 2007149832 A2 | 12/2007 | |
| WO | 2008056060 A2 | 5/2008 | |
| WO | 2008083118 A1 | 7/2008 | |
| WO | 2008094989 A2 | 8/2008 | |
| WO | 2009032328 A1 | 3/2009 | |
| WO | 2009035562 A2 | 3/2009 | |
| WO | 2009035565 A1 | 3/2009 | |
| WO | 2010008883 A1 | 1/2010 | |

(56) References Cited

FOREIGN PATENT DOCUMENTS

| WO | 2010096822 A2 | 8/2010 |
|---|---|---|
| WO | 2010085696 A9 | 6/2011 |

OTHER PUBLICATIONS

"U.S. Appl. No. 10/825,047, Response filed Apr. 22, 2009 to Non Final Office Actionmailed Oct. 22, 2008", 17 pgs.
"U.S. Appl. No. 10/825,047,Final Office Action mailed Jun. 9, 2009", 14 pgs.
"U.S. Appl. No. 11/695,537, Non Final Office Action mailed Sep. 18, 2009", 12 pgs.
"U.S. Appl. No. 11/695,537, Response filed Dec. 17, 2008 to Office Communicationmailed Nov. 28, 2008", 8 pgs.
"U.S. Appl. No. 11/695,537, Restriction Requirement mailed Oct. 3, 2008", 10 pgs.
"U.S. Appl. No. 11/695,545, Preliminary Amendment and Response filed Nov. 6, 2008 to Restriction Requirement mailed Oct. 6, 2008", 14 pgs.
"U.S. Appl. No. 11/695,545, Restriction Requirement mailed Oct. 6, 2008", 10 pgs.
"Assessment of Drug Concentrations in Tears in Therapeutic Drug Monitoring: I. Determination of Valproic Acid in Tears by Gas Chromatography/Mass Spectrometry With EC/NCI Mode", 716-722.
"Australian Application Serial No. 2007234445, Examiner Report mailed Oct. 12, 2009", 2 pgs.
"Australian Application Serial No. 2007234447, Examiner Report mailed Oct. 6, 2009", 3 pgs.
"Canadian Application Serial No. 2,648,066, Office Action dated Nov. 1, 2010".
"Chapter 25—Ocular Penetration Enhancers", 527-548.
"Chinese Application Serial No. 200580028979.2, First Office Action mailed Dec. 12, 2008", 7pgs.
"Chinese Application Serial No. 200780017166.2, Second Office Action dated Mar. 6, 2012".
"Controlled Release Veterinary Drug Delivery", 118 pgs.
"European Application No. 08330451.4. Examination Report dated Nov. 5, 2010".
"European Application Serial No. 05768122.3. Office Action mailed Mar. 31, 2009", 3 pgs.
"Influence of Benzalkonium Chloride on the Penetration of Latanoprost into Rabbit Aqueous Humor After Ocular Instillations, Other Description Mar. 4, 2015", 1 pg.
"International Application Serial No. PCT/US07/65792, International Written Opinion mailed Nov. 20, 2008", 5 pgs.
"International Application Serial No. PCT/US2007/065789, International Search Reportmailed Aug. 13, 2008", 3 pgs.
"International Application Serial No. PCT/US2007/065789, Written Opinion mailed Aug. 13, 2008", 5 pgs.
"International Application Serial No. PCT/US2007/065792, International Search Report mailed Nov. 20, 2008", 2 pgs.
"International Application Serial No. PCT/US2008/010479, International Search Report mailed Dec. 15, 2008," 6 pgs.
"International Application Serial No. PCT/US2008/010479, Written Opinion mailed Dec. 15, 2008," 7 pgs.
"International Application Serial No. PCT/US2008/010487, International SearchReport mailed May 25, 2009," 5 pgs.
"International Application Serial No. PCT/US2008/010487, Written Opinion mailed May 25, 2009," 8 pgs.
"Israeli Application Serial No. 194514, Notice of Defects dated Sep. 14, 2011".
"Israeli Application Serial No. 212114, Notice of Defects dated Sep. 12, 2011".
"Japanese Application Serial No. 2009-503334, Notice of Rejection dated Aug. 30, 2011".
"Japanese Application Serial No. 2009-503335, Decision of Rejection dated Apr. 3, 2012".
"Korean Application Serial No. 10-2008-7026758, Office Action dated Oct. 25, 2010".
"Korean Application Serial No. 10-2008-7026781, Office Action dated Aug. 26, 2010".
"Manufacture of Drug Cores for Sustained Release of Therapeutic Agent", 66 pgs.
"Nasolacrimal Drainage System Implants for Drug Delivery", 103 pgs.
"New Zealand Application Serial No. 571758, Examination Report dated May 24, 2010", 2 pgs.
"New Zealand Application Serial No. 571758, Examination Report dated Nov. 14, 2011".
"Permeability of Chemical Delivery Systems Across Rabbit Corneal (SIRC) Cell Line and Isolated Corneas: A Comparative Study, Other Description Mar. 4, 2015", 1 pg.
"Russian Application Serial No. 2010112426, Official Action dated Jun. 7, 2012", 15 pgs.
"Size Variation of the Lacrimal Punctum in Adults", 231-233.
"Treatment Medium Delivery Device and Methods for Delivery of Such Treatment Mediums to the Eye Using Such a Delivery Device", 33 pgs.
Agarwal, et al., "Garg Textbook of Opthalmology Ed.", New Dehli, Jaypee Brothers Medical Publishing, (2002), 39-42.
U.S. Appl. No. 10/825,047, Non-Final Office Action mailed Oct. 22, 2008, 13pgs.
U.S. Appl. No. 10/825,047, Response filed Aug. 18, 2008 to RestrictionRequirement mailed Jul. 17, 2008, 10 pgs.
U.S. Appl. No. 10/825,047, Response filed Oct. 22, 2009 to Final Office Actionmailed Jun. 9, 2009, 20 pgs.
U.S. Appl. No. 10/825,047, Restriction Requirement mailed Jul. 17, 2008, 6pgs.
U.S. Appl. No. 11/571,147, Restriction Requirement mailed Jun. 26, 2009, 5 pgs.
U.S. Appl. No. 11/695,537, Notice mailed Nov. 28, 2008 Regarding aNoncompliant or Nonresponsive Amendment filed on Nov. 3, 2008, 3 pgs.
U.S. Appl. No. 11/695,537, Response filed Nov. 3, 2008 to RestrictionRequirement mailed Oct. 3, 2008, 15 pgs.
U.S. Appl. No. 12/604,202, Preliminary Amendment filed Nov. 30, 2009, 6 pgs.
Blood vessel reference http://www.newworldencyclopedia.org/entry/Blood_vessel 2008.
Crisp, "Time Release Ophthalmic Drug Delivery Insert", Abstract for Grant No. 1R43EY012916-01; [Online]. Retrieved from the Internet:<http://crisp.cit.nih.gov.crisp/CRISP_LIB.getdoc?textkey+6073940&p_grant_num=1R43EY012916-01&p_query=&ticket=63935662&p_audit_session_id=325068793&p_keyWOrds=, 1 pg.
De Juan, Jr., E., et al., "Expandable Nasolacrimal Drainage Systemimplants", U.S. Appl. No. 60/970,696, filed Sep. 7, 2007, 82 pgs.
De Juan, Jr., E., et al., "Manufacture of Expandable Nasolacrimaldrainage System Implants", U.S. Appl. No. 60/970,720, filed Sep. 7, 2007, 57 pgs.
De Juan, Jr., E., et al., "Multiple Drug Delivery Systems Andcombinations of Drugs with Punctal Implants", U.S. Appl. No. 60/970,820, filed Sep. 7, 2007, 67 pgs.
Douni et al. Arthritis Research and Therapy 2004 6:R65-R72.
Drury et al. Biomaterials 2003 24:4337-4351.
Eisenberg et al. Survey of Ophthalmology 2002 47(Suppl 1): S105-S115.
European Application Serial No. 05768122.3, Office Action mailed on Apr. 17, 2009, 6pgs.
Final Written Decision in IPR 2019-00448 U.S. Pat. No. 9,849,082.
Fukano, Y., et al., "Influence of Benzalkonium Chloride on the Penetration ofLatanoprost into Rabbit Aqueous Humor After Ocular Instillations", AAPS Journal,vol. 8(S2), (Abstract No. 1397), 2006, 1 pg.
Goskonda, V. R., et al., "Permeability of Chemical Delivery Systems AcrossRabbit Corneal (SIRC) Cell Line and Isolated Corneas: A Comparative Study",Pharmaceutical Development and Technology, 5(3), (Abstract Only), Jul. 2000, 1 pg.
Oasis Product Catalog, Apr. 2009, 7 pgs.

(56) References Cited

OTHER PUBLICATIONS

Production Information for EaglePlug® TearFlow™, © 2009 EagleVision, Inc.,Memphis, TN, 2009, 1 pg.
Production Information for the Micro Flow™ Punctal Occluder, Odyssey Medical,2009, 1 pg.
Rathbone et al. Controlled Release Veterinary Drug Delivery: Biological and Pharmaceutical Considerations 2000 Amsterdam:Elsevier p. 118.
Weinreb, R.N., "Enhancement of scleral macromolecular permeability with prostaglandins", Trans Am Ophthalmol Soc. 2001; 99: 319-343.

* cited by examiner

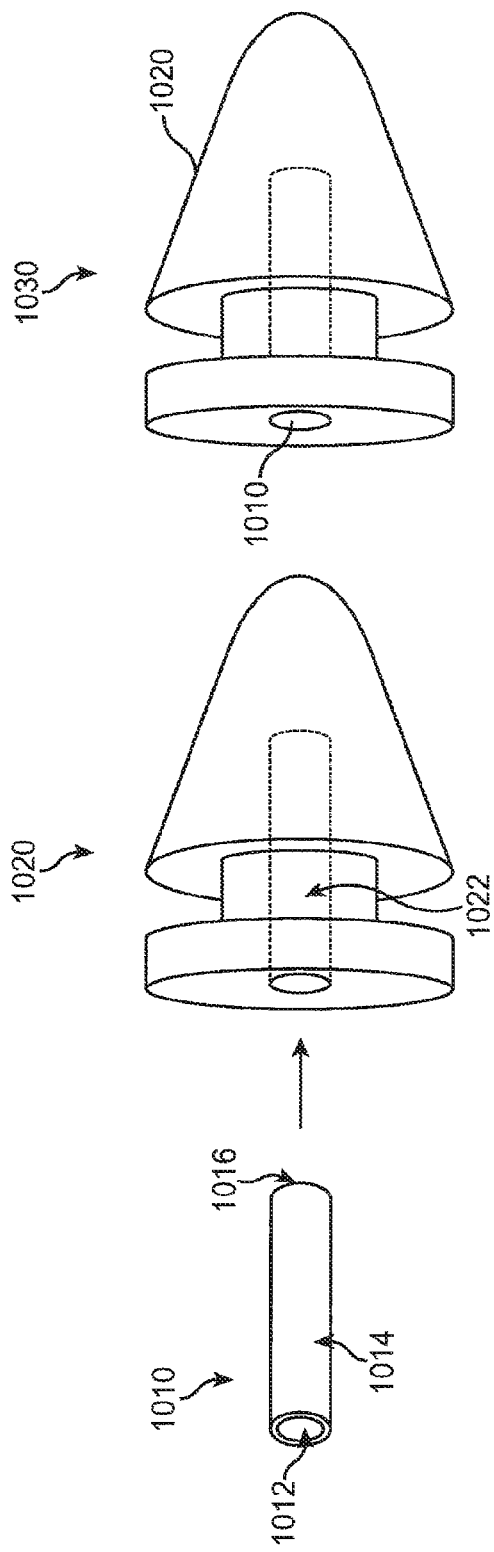

NASOLACRIMAL DRAINAGE SYSTEM IMPLANTS FOR DRUG THERAPY

CROSS-REFERENCE TO RELATED APPLICATIONS

This application is a continuation application of U.S. patent application Ser. No. 11/695,545, filed Apr. 2, 2007, which claims the benefit under 35 USC 119(e) of U.S. Provisional Application No. 60/787,775 filed on Mar. 31, 2006, and U.S. Provisional Application No. 60/871,864, filed on Dec. 26, 2006, the full disclosures of which are incorporated herein by reference.

BACKGROUND OF THE INVENTION

The present application is related to implants for use in or near the nasolacrimal drainage system, with embodiments providing canalicular implants, lacrimal sac implants, punctal plugs and punctal plugs with drug delivery capabilities.

A variety of challenges face patients and physicians in the area of ocular drug delivery. In particular, the repetitive nature of the therapies (multiple injections, instilling multiple eye drop regimens per day), the associated costs, and the lack of patient compliance may significantly impact the efficacy of the therapies available, leading to reduction in vision and many times blindness.

Patient compliance in taking the medications, for example instilling the eye drops, can be erratic, and in some cases, patients may not follow the directed treatment regime. Lack of compliance can include, failure to instill the drops, ineffective technique (instilling less than required), excessive use of the drops (leading to systemic side effects), and use of non-prescribed drops or failure to follow the treatment regime requiring multiple types of drops. Many of the medications may require the patient to instill them up to 4 times a day.

In addition to compliance, the cost of at least some eye drop medications is increasing, leading some patients on limited incomes to be faced with the choice of buying basic necessities or instead getting their prescriptions filled. Many times insurance does not cover the total cost of the prescribed eye drop medication, or in some cases eye drops containing multiple different medications.

Further, in many cases, topically applied medications have a peak ocular effect within about two hours, after which additional applications of the medications should be performed to maintain the therapeutic benefit. In addition, inconsistency in self-administered or ingested medication regimes can result in a suboptimal therapy. PCT Publication WO 06/014434 (Lazar), which is incorporated herein by reference in its entirety, may be relevant to these and/or other issues associated with eye drops.

One promising approach to ocular drug delivery is to place an implant that releases a drug in tissue near the eye. Although this approach can offer some improvement over eye drops, some potential problems of this approach may include implantation of the implant at the desire tissue location, retention of the implant at the desired tissue location, and sustaining release of the drug at the desired therapeutic level for an extended period of time. For example in the case of glaucoma treatment, undetected and premature loss of an implant can result in no drug being delivered, and the patient can potentially suffer a reduction in vision, possibly even blindness.

In light of the above, it would be desirable to provide improved drug delivery implants that overcome at least some of the above mentioned shortcomings.

BRIEF SUMMARY OF THE INVENTION

The present invention provides improved implant devices, systems and methods for insertion into a punctum of a patient. In many embodiments, the implant device can be reliably retained in the eye such that the therapeutic agent can be delivered for an extended period of time.

In a first aspect, embodiments of the present invention provide an implant for insertion into a punctum of a patient. The implant comprises a drug core having a distal end and a proximal end. The distal end of the drug core has a cross section suitable for insertion through a punctum. The drug core comprises a therapeutic agent deliverable into the eye. A sheath is disposed over a portion of the drug core to define at least one exposed surface of the drug core. The at least one exposed surface of the drug core can be located near the proximal end to contact a tear or tear film fluid and release the therapeutic agent at therapeutic levels over a sustained period when the implant is implanted for use.

In many embodiments, a retention structure is attached to the drug core to retain the drug core near and/or in the punctum. The retention structure may be attached to the drug core via the sheath. The retention structure can comprise a hydrogel adapted to expand when the retention structure is placed in the punctum. The retention structure can comprise an attachment member having an axially oriented surface. Expansion of the hydrogel can urge against the axially oriented surface to retain the hydrogel while the hydrogel is hydrated. The attachment member can comprise at least one of a protrusion, a flange, a rim, or an opening through a portion of the retention structure.

In many embodiments, the retention structure comprises a flange near the at least one exposed surface to retain the surface near the punctum. The retention structure may have a size suitable to fit at least partially within the canalicular lumen. The retention structure can be expandable between a small profile configuration suitable for insertion and a large profile configuration to anchor the retention structure in the lumen, and the retention structure can be attached near the distal end of the drug core. In specific embodiments, the retention structure can slide along the drug core near the proximal end when the retention structure expands from the small profile configuration to the large profile configuration. A length of the retention structure along the drug core can be shorter in the large profile configuration than the small profile configuration.

In some embodiments, the retention structure is resiliently expandable. The small profile may have a cross section of no more than about 0.2 mm, and the large profile may have a cross section of no more than about 2.0 mm. The retention structure may comprise a tubular body having arms separated by slots. An occlusive element can be mounted to and expandable with the retention structure to inhibit tear flow. The retention structure can be disposed at least partially over the drug core. An occlusive element may inhibit tear flow through the lumen, and the occlusive element may cover at least a portion of the retention structure to protect the lumen from the retention structure.

In many embodiments, the sheath body may comprise a layer disposed over the drug core to inhibit release of the therapeutic agent through the layer. The drug core can release the therapeutic agent through the exposed surface. The drug core may releases the therapeutic agent at therapeutic levels throughout a time period of at least one week when the implant is implanted with the surface exposed to the tear or tear film fluid. The drug core can comprise inclusions of the agent and the agent is soluble in the drug core to provide a substantially uniform release rate when the drug core is implanted.

In some embodiments, an occlusive element may inhibit tear fluid flow through the canalicular lumen. For example, the occlusive element can shaped to block tear flow through the canalicular lumen.

In many embodiments, an implant for insertion into a punctum of a patient is provided. The implant comprises a therapeutic agent, and a material to hold the therapeutic agent. A retention structure is disposed over at least a portion of the material, and the retention structure is expandable from the material to retain the material near the punctum.

In many embodiments, the material holds the therapeutic agent in at least one of a reservoir or a matrix. An occlusive element may be supported by the retention structure. The retention structure may be expandable between a small profile configuration suitable for insertion and a large profile configuration to anchor the retention structure in the lumen, and the occlusive element may expand with the retention structure.

In another aspect, embodiments of the present invention provide a method of treating an eye with a therapeutic agent. The method comprises inserting a retention structure and a distal end of a drug core of an implant into a punctum. A therapeutic agent is delivered from the drug core to the eye. An exposed surface of the drug core is limited near the proximal end of the drug core with a sheath. The exposed surface may contact the tear or tear film fluid such that the treatment agent migrates from the exposed surface to the eye over a sustained period while the drug core is retained near the punctum by the retention structure.

In many embodiments, a method of treating an eye with a therapeutic agent is provided. The method comprises inserting a retention structure and a distal end of a drug core through a punctum so that the drug core is retained near the punctum. The drug core comprises a therapeutic agent deliverable to the eye and wherein an exposed surface of the drug core located near the proximal end of the drug core. The exposed surface contacts the tear or tear film fluid and the treatment agent migrates from the exposed surface to the eye over a sustained period while the drug core is retained near the punctum.

In many embodiments, the retention structure expands from a narrow profile configuration to a wide profile configuration. The retention structure hydrates when inserted through the punctum to expand from a narrow profile configuration to a wide profile configuration.

In many embodiments, a method of treating an eye with a therapeutic agent is provided, the method comprises inserting a retention structure through a punctum into a canalicular lumen so that a drug core is anchored to the lumen with the retention structure and releases effective amounts of a therapeutic agent into a tear or tear film fluid of the eye. The drug core is removed from the retention structure while the retention structure remains anchored to the lumen. A replacement drug core is attached to the retention structure while the retention structure remains anchored to the lumen. At least one exposed surface of the replacement drug core releases the therapeutic agent at therapeutic levels over a sustained period.

In many embodiments, a method for treating an eye is provided. The method comprises inserting a distal end of an implant into a punctum. A retention structure of the implant is expanded so as to inhibit expulsion of the implant. The expansion of the implant helps to occlude a flow of tear fluid through the punctum. A therapeutic agent is delivered from a proximal end of the implant to the tear fluid adjacent the eye. Delivery of the therapeutic agent is inhibited distally of the proximal end.

In many embodiments, delivery of the therapeutic agent to the tear is inhibited with a sheath having a portion exposed to the tear fluid. In specific embodiments, the retention structure may comprise a superelastic or shape memory alloy. The retention structure comprise a hydrogel and extends distally of the drug core.

In another aspect many embodiments of the present invention provide an implant for treating an eye. The eye has a tear fluid and a punctum. The implant comprises a drug core having a proximal end, a distal end, and a cross section suitable for insertion into the punctum. A sheath is disposed over the drug core distally of the proximal end. A swellable material is disposed distally of the proximal end. The swellable material is adapted to swell after insertion into the punctum to retain the drug core and occlude the tears in fluid communication with the drug core.

In many embodiments, wings are connected to the sheath near the proximal end of the drug core. The wings can be sized to remain outside the punctum so as to retain the proximal end of the drug core near the punctum.

In many embodiments, an implant for treating an eye is provided. The eye has a tear fluid and a punctum. The implant comprises a drug core having a proximal end, a distal end, and a cross section suitable for insertion into the punctum. A sleeve is disposed over the drug core at least distally of the proximal end. A swellable material is disposed distally of the proximal end and at least partially covered by the sleeve. The swellable material is adapted to swell after insertion into the punctum to retain the drug core and occlude the tears in fluid communication with the drug core.

In many embodiments, the sleeve comprises tabs to retain the punctal plug upon expansion of the swellable material.

In many embodiments, a punctal plug for treating an eye is provided. The eye has a tear fluid and a punctum. The plug comprises a plug body, and a drug core inside the plug body. The drug core comprises a mixture of therapeutic agent and a matrix. A surface of the core is exposed to the tear fluid to treat the eye.

In specific embodiments, the drug core is capable of resilient expansion to accommodate a needle inserted therein while the plug is inserted into a punctum of the eye.

In many embodiments, a punctal plug for treating an eye is provided. The eye has a tear fluid and a punctum. The plug comprises an expandable retention element to expand and engage the punctum when positioned in the eye. A body is connected to the expandable retention element and comprises a protrusion for removal of the retention element from the punctum.

In many embodiments, the expandable retention element comprises a swellable material and the body is adapted to retain the swellable material while the body is removed. In specific embodiments, the swellable material may comprise a hydrogel.

BRIEF DESCRIPTION OF THE DRAWINGS

FIG. 10A shows a drug core insert for use with a punctal plug, according to embodiments of the present invention;

FIG. 10B shows a punctal plug comprising an internal cavity with a cylindrical shape, according to embodiments of the present invention;

FIG. 10C shows a punctal plug as in FIG. 10B with a drug core as in FIG. 10A inserted therein, according to embodiments of the present invention;

DETAILED DESCRIPTION OF THE INVENTION

Figure 1:
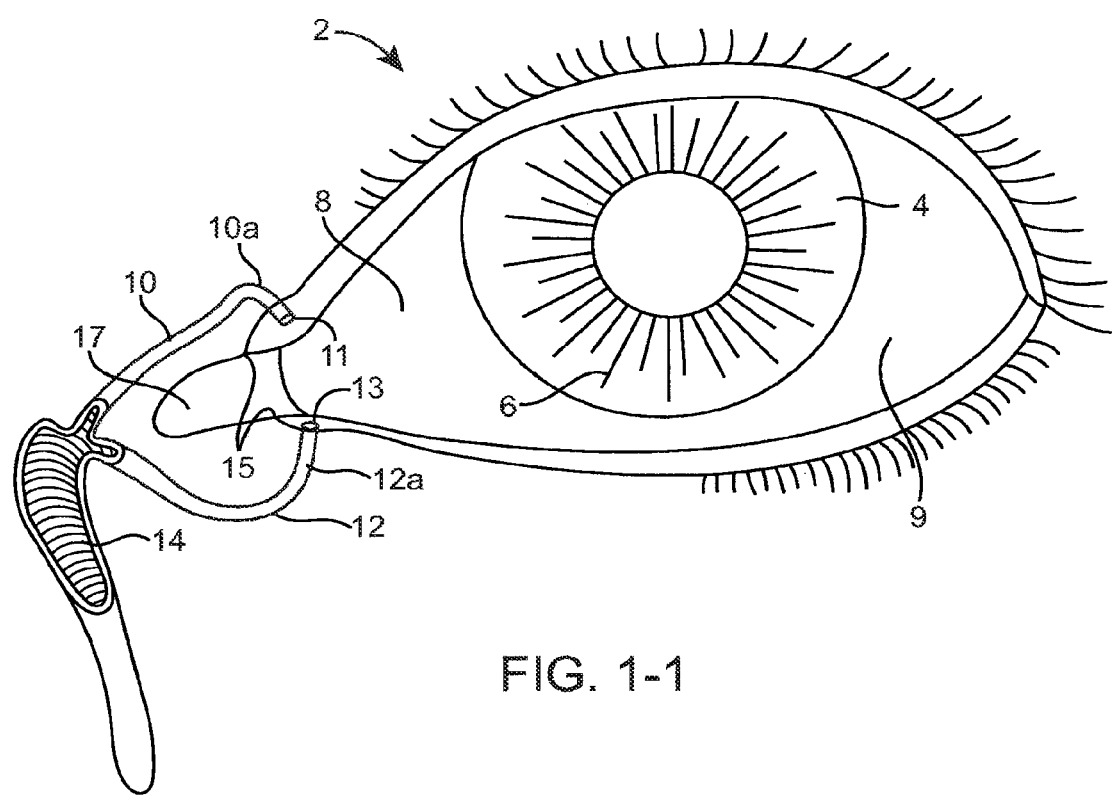
FIGS. 1-1 and 1-2 show anatomical tissue structures of the eye suitable for use with implants, according to embodiments of the present invention.
Figures 1, 2:
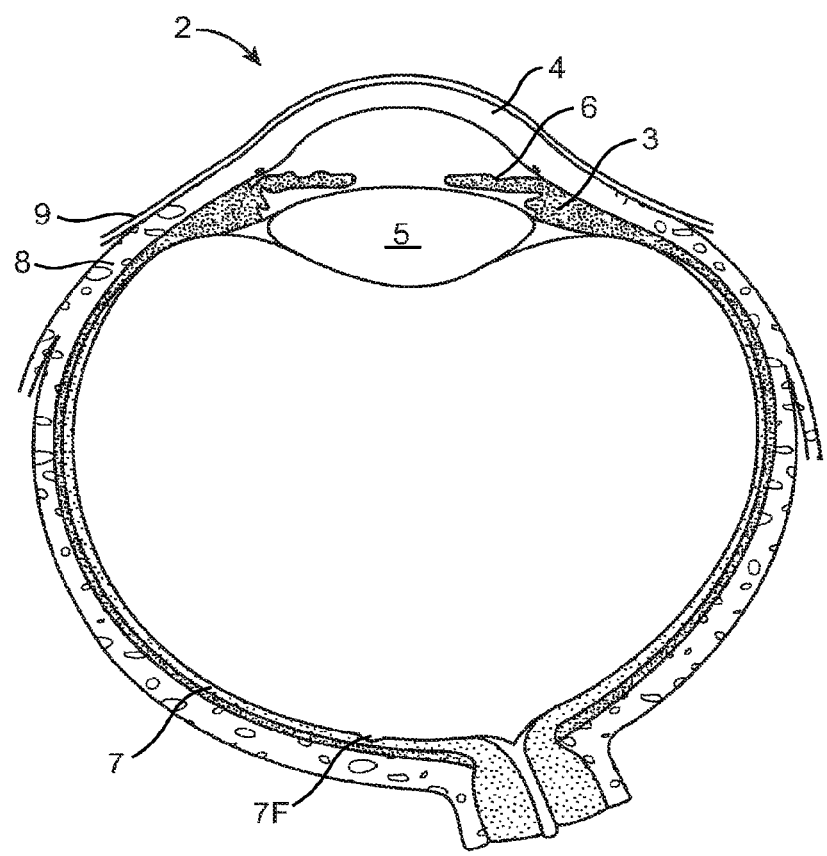

FIGS. 1-1 and 1-2 show anatomical tissue structures of an eye 2 suitable for treatment with implants, according to an embodiment of the present invention. Eye 2 includes a cornea 4 and an iris 6. A sclera 8 surrounds cornea 4 and iris 6 and appears white. A conjunctival layer 9 is substantially transparent and disposed over sclera 8. A crystalline lens 5 is located within the eye. A retina 7 is located near the back of eye 2 and is generally sensitive to light. Retina 7 includes a fovea 7F that provides high visual acuity and color vision. Cornea 4 and lens 5 refract light to form an image on fovea 7F and retina 7. The optical power of cornea 4 and lens 5 contribute to the formation of images on fovea 7F and retina 7. The relative locations of cornea 4, lens 5 and fovea 7F are also important to image quality. For example, if the axial length of eye 2 from cornea 4 to retina 7F is large, eye 2 can be myopic. Also, during accommodation, lens 5 moves toward cornea 4 to provide good near vision of objects proximal to the eye.

The anatomical tissue structures shown in FIG. 1-1 also include the lacrimal system, which includes an upper canaliculus 10 and a lower canaliculus 12, collectively the canaliculae, and the naso-lacrimal duct or sac 14. The upper and lower canaliculae terminate in an upper punctum 11 and a lower punctum 13, also referred to as punctal apertures. The punctal apertures are situated on a slight elevation at the medial end of the lid margin at the junction 15 of the ciliary and lacrimal portions near the medial canthus 17. The punctal apertures are round or slightly ovoid openings surrounded by a connective ring of tissue. Each of the punctal openings 11, 13 leads into a vertical portion 10a, 12a of the respective canaliculus before turning horizontally to join its other canaliculus at the entrance of a lacrimal sac 14. The canaliculae are tubular and lined by stratified squamous epithelium surrounded by elastic tissue which permits the canaliculus to be dilated.

Figure 1A:
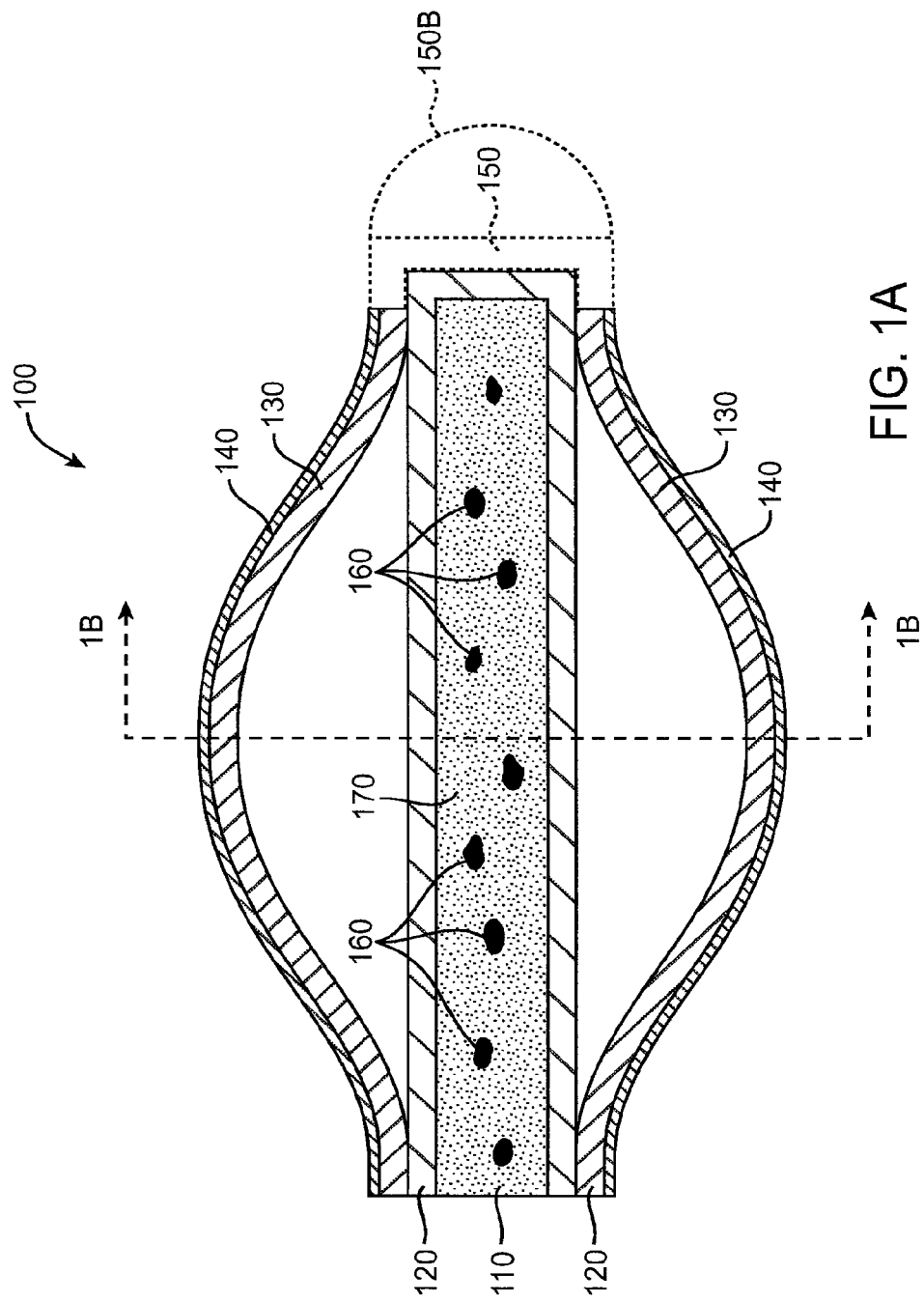
FIG. 1A shows a top cross sectional view of a sustained release implant to treat an optical defect of an eye, according to an embodiment of the present invention.

FIG. 1A shows a top cross sectional view of a sustained release implant 100 to treat an optical defect of an eye, according to embodiments of the present invention. Implant 100 includes a drug core 110. Drug core 110 is an implantable structure that retains a therapeutic agent. Drug core 110 comprises a matrix 170 that contains inclusions 160 of therapeutic agent. Inclusions 160 will often comprise a concentrated form of the therapeutic agent, for example a crystalline form of the therapeutic agent, and the therapeutic agent may over time dissolve into matrix 170 of drug core 110. Matrix 170 can comprise a silicone matrix or the like, and the mixture of therapeutic agent within matrix 170 can be non-homogeneous. In many embodiments, the non-homogenous mixture comprises a silicone matrix portion that is saturated with the therapeutic agent and an inclusions portion comprising inclusions of the therapeutic agent, such that the non-homogenous mixture comprises a multiphase non-homogenous mixture. In some embodiments, inclusions 160 comprise droplets of an oil of the therapeutic agent, for example Latanoprost oil. In some embodiments, inclusions 160 may comprise particles of the therapeutic agent, for example solid Bimatoprost particles in crystalline form. In many embodiments, matrix 170 encapsulates inclusions 160, and inclusions 160 may comprise microparticles have dimensions from about 1 μm to about 100 μm. The encapsulated inclusions dissolve into the surrounding solid matrix, for example silicone, that encapsulates the micro particles such that matrix 170 is substantially saturated with the therapeutic agent while the therapeutic agent is released from the core.

Drug core 110 is surrounded by a sheath body 120. Sheath body 120 is can be substantially impermeable to the therapeutic agent, so that the therapeutic agent is often released from an exposed surface on an end of drug core 110 that is not covered with sheath body 120. A retention structure 130 is connected to drug core 110 and sheath body 120. Retention structure 130 is shaped to retain the implant in a hollow tissue structure, for example, a punctum of a canaliculus as described above.

An occlusive element 140 is disposed on and around retention structure 130. Occlusive element 140 is impermeable to tear flow and occludes the hollow tissue structure and may also serve to protect tissues of the tissue structure from retention structure 130 by providing a more benign tissue-engaging surface. Sheath body 120 includes a sheath body portion 150 that connects to retention structure 130 to retain sheath body 120 and drug core 110. Sheath body portion 150 can include a stop to limit movement of sheath body 120 and drug core 110. In many embodiments, sheath body portion 150 can be formed with a bulbous tip 150B. Bulbous tip 150B can comprise a convex rounded external portion that provides atraumatic entry upon 11 introduction into the canaliculus. In many embodiments, sheath body portion 150B can be integral with occlusive element 140.

Figure 1B:
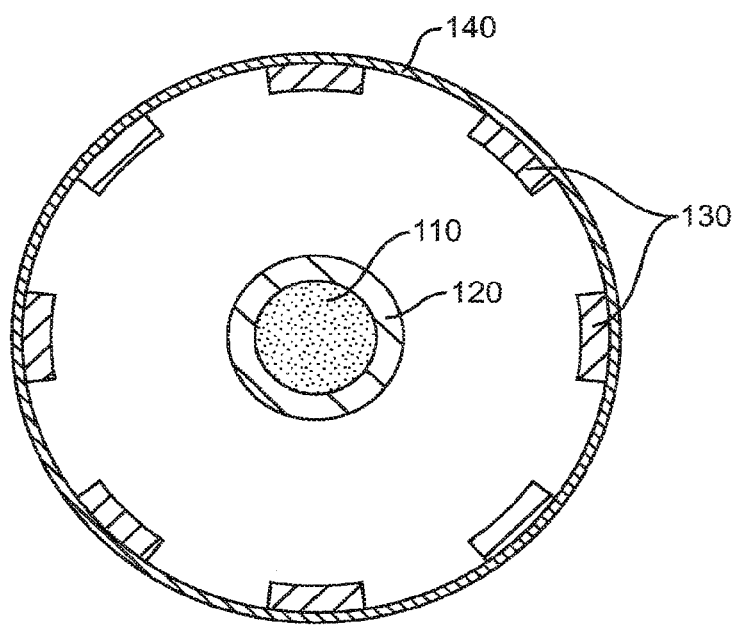
FIG. 1B shows a side cross sectional view of the sustained release implant of FIG. 1A.

FIG. 1B shows a side cross sectional view of the sustained release implant of FIG. 1A. Drug core 110 is cylindrical and shown with a circular cross-section. Sheath body 120 comprises an annular portion disposed on drug core 110. Retention structure 130 comprises several longitudinal struts 131. Longitudinal struts 131 are connected together near the ends of the retention structure. Although longitudinal struts are shown, circumferential struts can also be used. Occlusive element 140 is supported by and disposed over longitudinal struts 131 of retention structure 130 and may comprise a radially expandable membrane or the like.

Figure 1C:
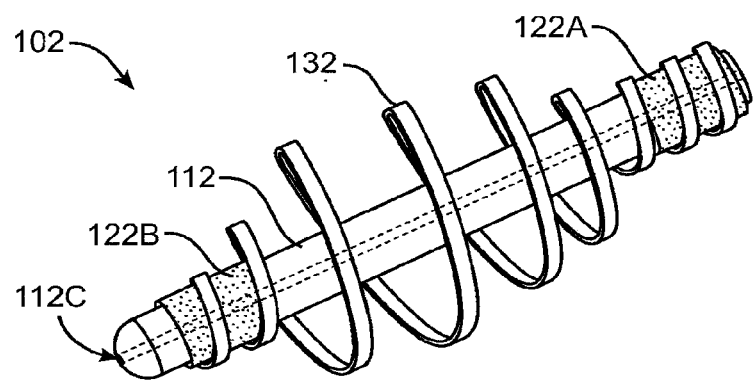
FIG. 1C shows a perspective view of a sustained release implant with a coil retention structure, according to an embodiment of the present invention.

FIG. 1C shows a perspective view of a sustained release implant 102 with a coil retention structure 132, according to an embodiment of the present invention. Retention structure 132 comprises a coil and retains a drug core 112. A lumen, for example channel 112C, may extend through the drug core 112 to permit tear flow through the lumen for the delivery of therapeutic agent for nasal and systemic applications of the therapeutic agent. In addition or in combination with channel 112C, retention structure 132 and core 112 can be sized to permit tear flow around the drug core and sheath body while the retention element holds tissue of the canaliculus away from the drug core. Drug core 112 may be partially covered. The sheath body comprises a first component 122A that covers a first end of drug cove 112 and a second component 122B that covers a second end of the drug core. An occlusive element can be placed over the retention structure and/or the retention structure can be dip coated as described above.

Figure 1D:
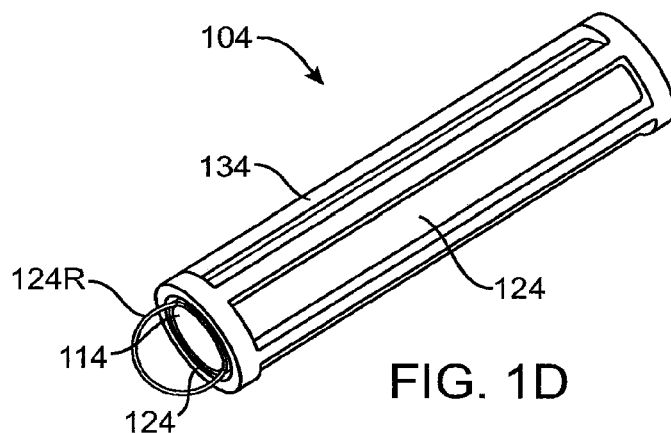
FIG. 1D shows a perspective view of a sustained release implant with a retention structure comprising struts, according to an embodiment of the present invention.

FIG. 1D shows a perspective view of a sustained release implant 104 with a retention structure 134 comprising struts, according to an embodiment of the present invention. Retention structure 134 comprises longitudinal struts and retains a drug core 114. Drug core 114 is covered with a sheath body 124 over most of drug core 114. The drug core releases therapeutic agent through an exposed end and sheath body 124 is annular over most of the drug core as described above. An occlusive element can be placed over the retention structure or the retention structure can be dip coated as described above. A protrusion that can be engaged with an instrument, for example a hook, a loop, a suture, or ring 124R, can extend from sheath body 124 to permit removal of the drug core and sheath body together so as to facilitate replacement of the sheath body and drug core while the retention structure remains implanted in the canaliculus. In some embodiments, a protrusion that can be engaged with an instrument comprising hook, a loop, a suture or a ring, can extend from retention structure 134 to permit removal of the sustained release implant by removing the retention structure with the protrusion, drug core and sheath body.

Figure 1E:
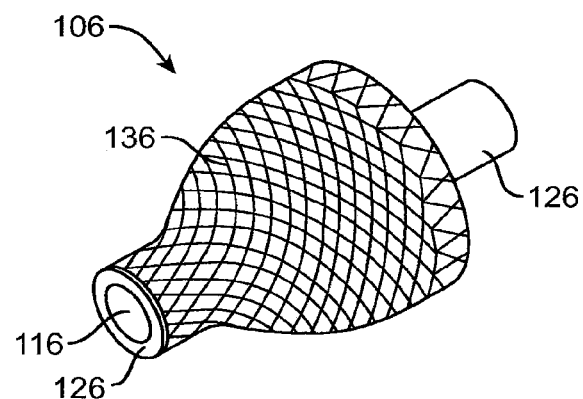
FIG. 1E shows a perspective view of a sustained release implant with a cage retention structure, according to an embodiment of the present invention.

FIG. 1E shows a perspective view of a sustained release implant 106 with a cage retention structure 136, according to an embodiment of the present invention. Retention structure 136 comprises several connected strands of metal and retains a drug core 116. Drug core 116 is covered with a sheath body 126 over most of drug core 116. The drug core releases therapeutic agent through an exposed end and sheath body 126 is annular over most of the drug core as described above. An occlusive element can be placed over the retention structure or the retention structure can be dip coated as described above.

Figure 1F:
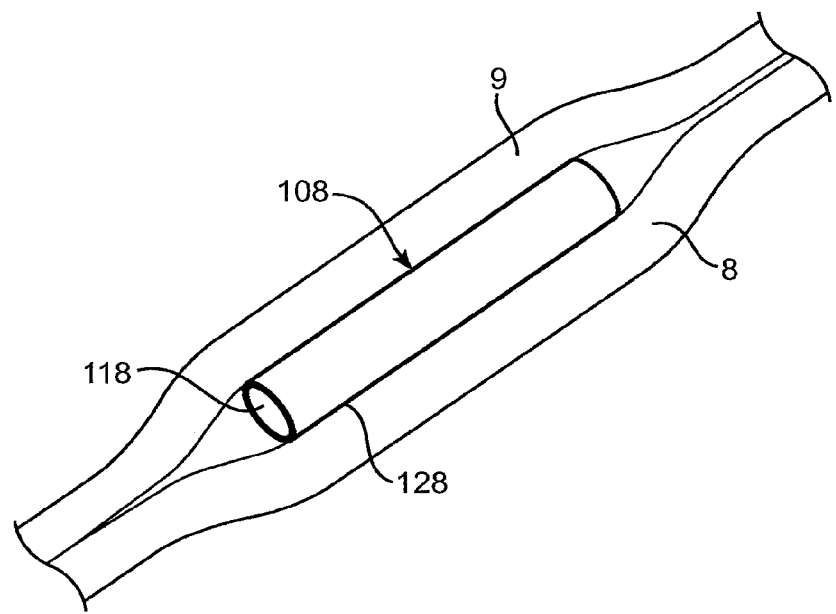
FIG. 1F shows a perspective view of a sustained release implant comprising a core and sheath, according to an embodiment of the present invention.

FIG. 1F shows a perspective view of a sustained release implant comprising a core and sheath, according to an embodiment of the present invention. Drug core 118 is covered with a sheath body 128 over most of drug core 118. The drug core releases therapeutic agent through an exposed end and sheath body 128 is annular over most of the drug core as described above. The rate of therapeutic agent release is controlled by the surface area of the exposed drug core and materials included within drug core 118. In many embodiments, the rate of elution of the therapeutic agent is strongly and substantially related to the exposed surface area of the drug core and weakly dependent on the concentration of drug disposed in the inclusions in the drug core. For circular exposed surfaces the rate of elution is strongly dependent on the diameter of the exposed surface, for example the diameter of an exposed drug core surface near an end of a cylindrical drug core. Such an implant can be implanted in ocular tissues, for example below conjunctival tissue layer 9 of the eye and either above sclera tissue layer 8, as shown in FIG. 1F, or only partially within the scleral tissue layer so as not to penetrate the scleral tissue. It should be noted that drug core 118 can be used with any of the retention structures and occlusive elements as described herein.

In an embodiment, the drug core is implanted between sclera 8 and conjunctiva 9 without sheath body 128. In this embodiment without the sheath body, the physical characteristics of the drug core can be adjusted to compensate for the increased exposed surface of drug core, for example by reducing the concentration of dissolved therapeutic agent in the drug core matrix as described herein.

Figure 1G:
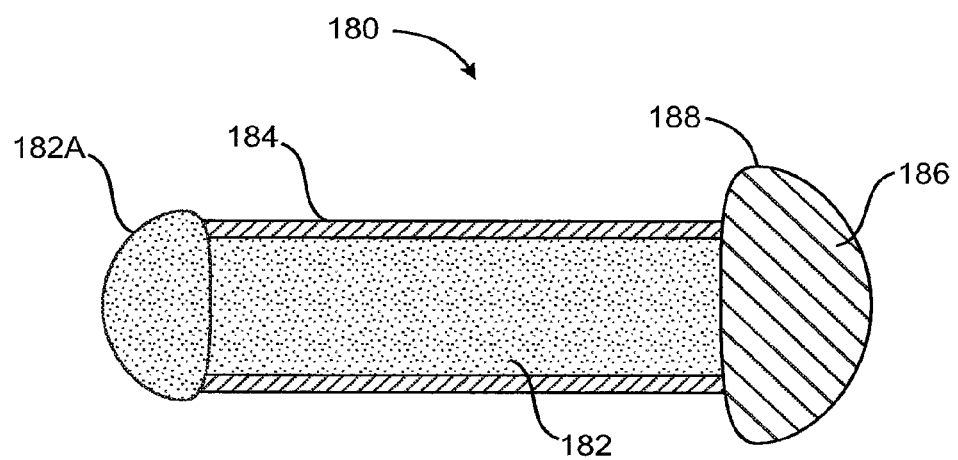
FIG. 1G schematically illustrates a sustained release implant comprising a flow restricting retention element, a core and a sheath, according to an embodiment of the present invention.

FIG. 1G schematically illustrates a sustained release implant 180 comprising a flow restricting retention structure 186, a core 182 and a sheath 184, according to an embodiment of the present invention. Sheath body 184 can at least partially cover drug core 182. Drug core 182 may contain particles of the therapeutic agent therein to provide a sustained release of the therapeutic agent. Drug core 182 can include an exposed convex surface area 182A. Exposed convex surface area 182A may provide an increased surface area to release the therapeutic agent. An occlusive element 188 can be disposed over retention structure 186 to block the flow of tear through the canaliculus. In many embodiments, retention structure 186 can be located within occlusive structure 188 to provide the occlusive element integrated with the retention structure. Flow restricting retention structure 186 and occlusive element 188 can be sized to block tear flow through the canaliculus.

The cores and sheath bodies described herein can be implanted in a variety of tissues in several ways. Many of the cores and sheaths described herein, in particular the structures described with reference to FIGS. 2A to 2J can be implanted alone as punctal plugs. Alternatively, many of the cores and sheath bodies described herein can comprise a drug core, sheath body, and/or the like so as to be implanted with the retention structures and occlusive elements described herein.

Figure 2A:
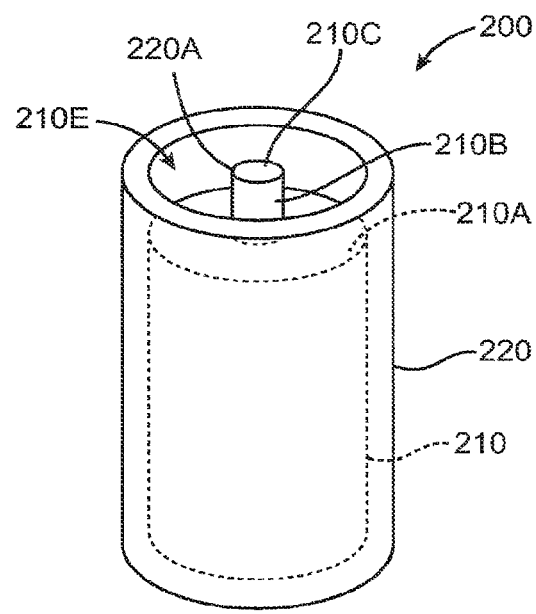
FIG. 2A shows a cross sectional view of a sustained release implant with core comprising an enlarged exposed surface area, according to an embodiment of the present invention.

FIG. 2A shows a cross sectional view of a sustained release implant 200 with core comprising an enlarged exposed surface area, according to an embodiment of the present invention. A drug core 210 is covered with a sheath body 220. Sheath body 220 includes an opening 220A. Opening 220 has a diameter that approximates the maximum cross sectional diameter of drug core 210. Drug core 210 includes an exposed surface 210E, also referred to as an active surface. Exposed surface 210E includes 3 surfaces: an annular surface 210A, a cylindrical surface 210B and an end surface 210C. Annular surface 210A has an outer diameter that approximates the maximum cross sectional diameter of core 210 and an inner diameter that approximates the outer diameter of cylindrical surface 210B. End surface 210C has a diameter that matches the diameter of cylindrical surface 210B. The surface area of exposed surface 210E is the sum of the areas of annular surface 210A, cylindrical surface 210B and end surface 210C. The surface area may be increased by the size of cylindrical surface area 210B that extends longitudinally along an axis of core 210.

Figure 2B:
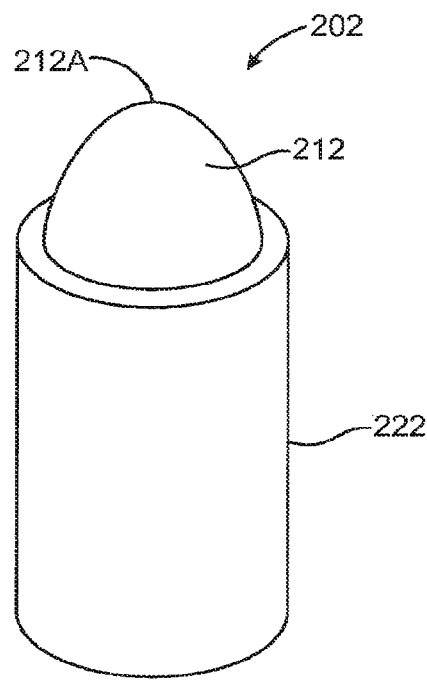
FIG. 2B shows a cross sectional view of a sustained release implant with a core comprising an enlarged exposed surface area, according to an embodiment of the present invention.

FIG. 2B shows a cross sectional view of a sustained release implant 202 with a core 212 comprising an enlarged exposed surface area 212A, according to an embodiment of the present invention. A sheath body 222 extends over core 212. The treatment agent can be released from the core as described above. Exposed surface area 212A is approximately conical, can be ellipsoidal or spherical, and extends outward from the sheath body to increase the exposed surface area of drug core 212.

Figure 2C:
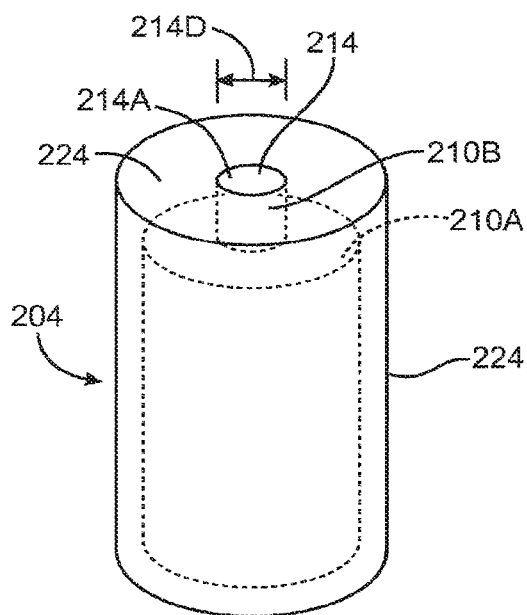
FIGS. 2C and 2D show perspective view and cross sectional views, respectively, of a sustained release implant with a core comprising a reduced exposed surface area, according to an embodiment of the present invention.
Figure 2D:
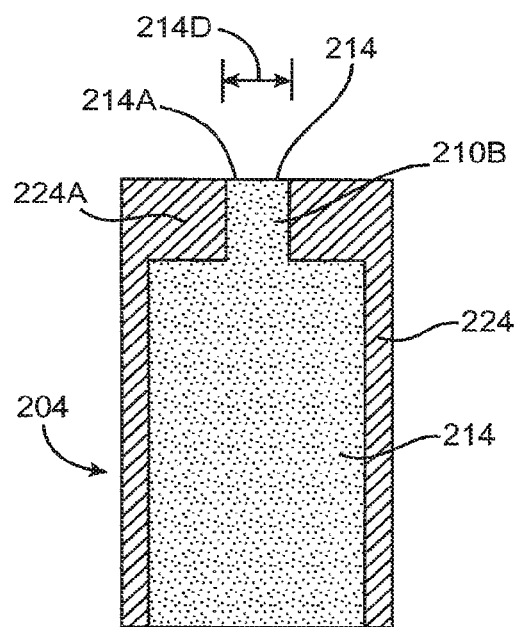

FIGS. 2C and 2D show perspective and cross sectional views, respectively, of a sustained release implant 204 with a drug core 214 comprising a reduced exposed surface area 214A, according to an embodiment of the present invention. Drug core 214 is enclosed within a sheath body 224. Sheath body 22 includes an annular end portion 224A that defines an opening through which drug core 214 extends. Drug core 214 includes an exposed surface 214A that releases the therapeutic agent. Exposed surface 214A has a diameter 214D that is less than a maximum dimension, for example a maximum diameter, across drug core 214.

Figure 2E:
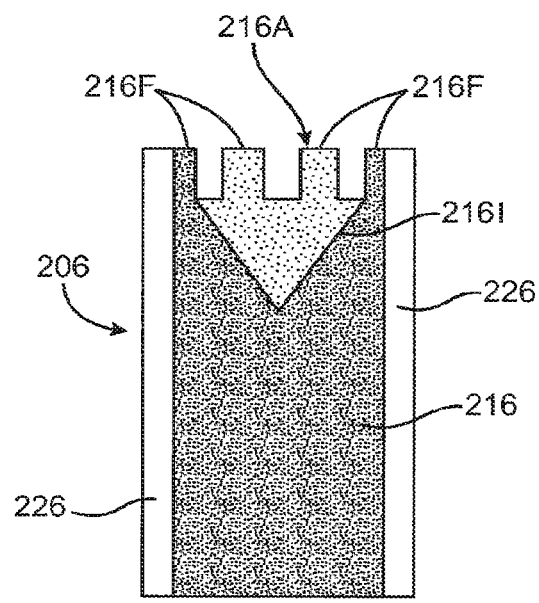
FIG. 2E shows a cross sectional view of a sustained release implant with a core comprising an enlarged exposed surface area with an indentation and castellation, according to an embodiment of the present invention.

FIG. 2E shows a cross sectional view of a sustained release implant 206 with a drug core 216 comprising an enlarged exposed surface area 216A with castellation extending therefrom, according to an embodiment of the present invention. The castellation includes several spaced apart fingers 216F to provide increased surface area of the exposed surface 216A. In addition to increased surface area provided by castellation, drug core 216 may also include an indentation 216I. Indentation 216I may have the shape of an inverted cone. Core 216 is covered with a sheath body 226. Sheath body 226 is open on one end to provide an exposed surface 216A on drug core 216. Sheath body 226 also includes fingers and has a castellation pattern that matches core 216.

Figure 2F:
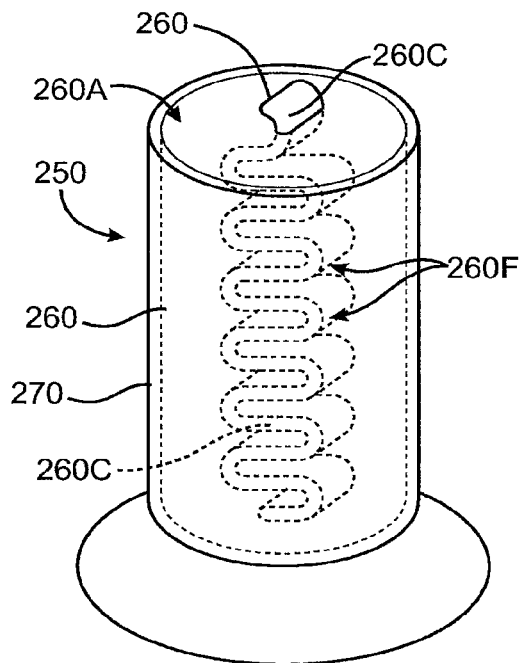
FIG. 2F shows a perspective view of a sustained release implant comprising a core with folds, according to an embodiment of the present invention.

FIG. 2F shows a perspective view of a sustained release implant 250 comprising a core with folds, according to an embodiment of the present invention. Implant 250 includes a core 260 and a sheath body 270. Core 260 has an exposed surface 260A on the end of the core that permits drug migration to the surrounding tear or tear film fluid. Core 260 also includes folds 260F. Folds 260F increase the surface area of core that is exposed to the surrounding fluid tear or tear film fluid. With this increase in exposed surface area, folds 260F increase migration of the therapeutic agent from core 260 into the tear or tear film fluid and target treatment area. Folds 260F are formed so that a channel 260C is formed in core 260. Channel 260C connects to the end of the core to an opening in exposed surface 260A and provides for the migration of treatment agent. Thus, the total exposed surface area of core 260 includes exposed surface 260A that is directly exposed to the tear or tear film fluid and the surfaces of folds 260F that are exposed to the tear or tear film fluids via connection of channel 260C with exposed surface 260A and the tear or tear film fluid.

Figure 2G:
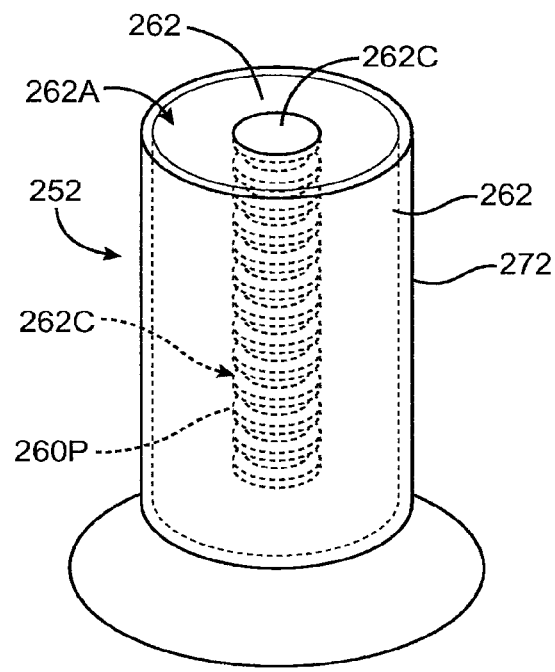
FIG. 2G shows a perspective view of a sustained release implant with a core comprising a channel with an internal porous surface, according to an embodiment of the present invention.

FIG. 2G shows a perspective view of a sustained release implant with a core comprising a channel with an internal porous surface, according to an embodiment of the present invention. Implant 252 includes a core 262 and sheath body 272. Core 262 has an exposed surface 262A on the end of the core that permits drug migration to the surrounding tear or tear film fluid. Core 262 also includes a channel 262C. Channel 262C increases the surface area of the channel with a porous internal surface 262P formed on the inside of the channel against the core. Channel 262C extends to the end of the core near exposed surface 262A of the core. The surface area of core that is exposed to the surrounding tear or tear film fluid can include the inside of core 262 that is exposed to channel 262C. This increase in exposed surface area can increase migration of the therapeutic agent from core 262 into the tear or tear film fluid and target treatment area. Thus, the total exposed surface area of core 262 can include exposed surface 260A that is directly exposed to the tear or tear film fluid and porous internal surface 262P that is exposed to the tear or tear film fluids via connection of channel 262C with exposed surface 262A and the tear or tear film fluid.

Figure 2H:
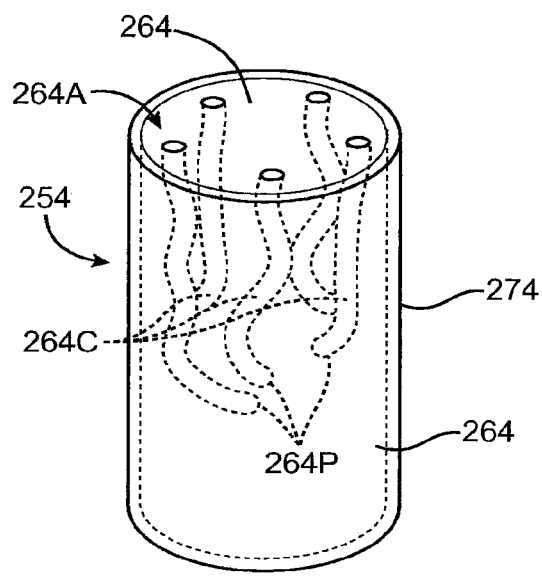
FIG. 2H shows a perspective view of a sustained release implant with a core comprising porous channels to increase drug migration, according to an embodiment of the invention.

FIG. 2H shows a perspective view of a sustained release implant 254 with a core 264 comprising channels to increase drug migration, according to an embodiment of the invention. Implant 254 includes core 264 and sheath body 274. Exposed surface 264A is located on the end of core 264, although the exposed surface can be positioned at other locations. Exposed surface 264A permits drug migration to the surrounding tear or tear film fluid. Core 264 also includes channels 264C. Channels 264C extend to exposed surface 264. Channels 264C are large enough that tear or tear film fluid can enter the channels and therefore increase the surface area of core 264 that is in contact with tear or tear film fluid. The surface area of the core that is exposed to the surrounding fluid tear or tear film fluid includes the inner surfaces 264P of core 262 that define channels 264C. With this increase in exposed surface area, channels 264C increase migration of the therapeutic agent from core 264 into the tear or tear film fluid and target treatment area. Thus, the total exposed surface area of core 264 includes exposed surface 264A that is directly exposed to the tear or tear film fluid and internal surface 264P that is exposed to the tear or tear film fluids via connection of channels 262C with exposed surface 264A and the tear or tear film fluid.

Figure 2I:
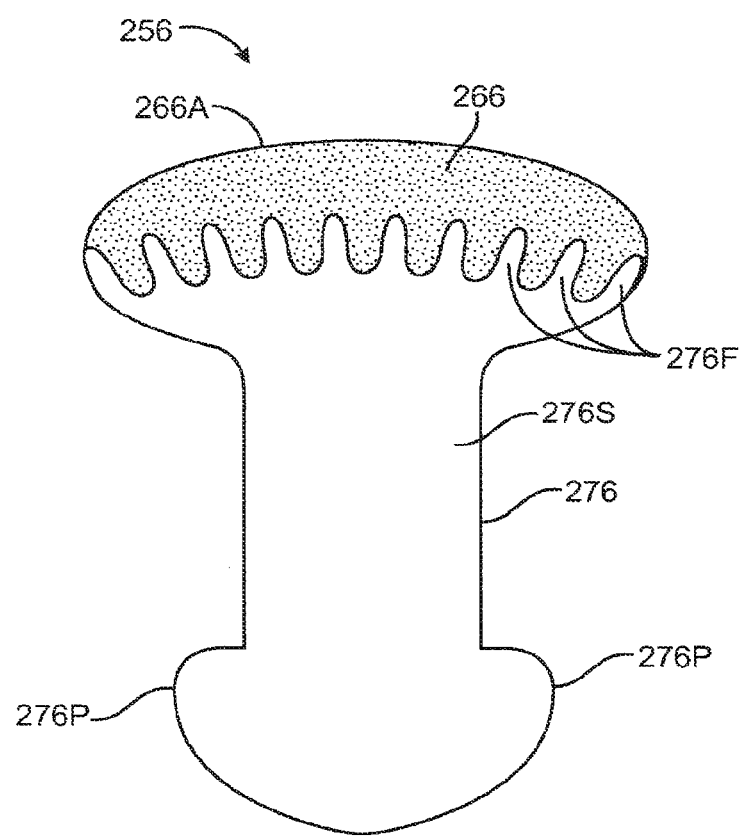
FIG. 2I shows a perspective view of a sustained release implant with a convex exposed drug core surface, according to an embodiment of the present invention.

FIG. 2I shows a perspective view of a sustained release implant 256 with a drug core 266 comprising a convex exposed surface 266A, according to an embodiment of the present invention. Drug core 266 is partially covered with a sheath body 276 that extends at least partially over drug core 266 to define convex exposed surface 266A. Sheath body 276 comprises a shaft portion 276S. Convex exposed surface 266A provides an increased exposed surface area above the sheath body. A cross sectional area of convex exposed surface 266A is larger than a cross sectional area of shaft portion 276S of sheath body 276. In addition to the larger cross sectional area, convex exposed surface 266A has a larger surface area due to the convex shape 16 which extends outward from the core. Sheath body 276 comprises several fingers 276F that support drug core 266 in the sheath body and provide support to the drug core to hold drug core 266 in place in sheath body 276. Fingers 276F are spaced apart to permit drug migration from the core to the tear or tear film fluid between the fingers. Protrusions 276P extend outward on sheath body 276. Protrusions 276P can be pressed inward to eject drug core 266 from sheath body 276. Drug core 266 can be replaced with another drug core after an appropriate time, for example after drug core 266 has released most of the therapeutic agent.

Figure 2J:
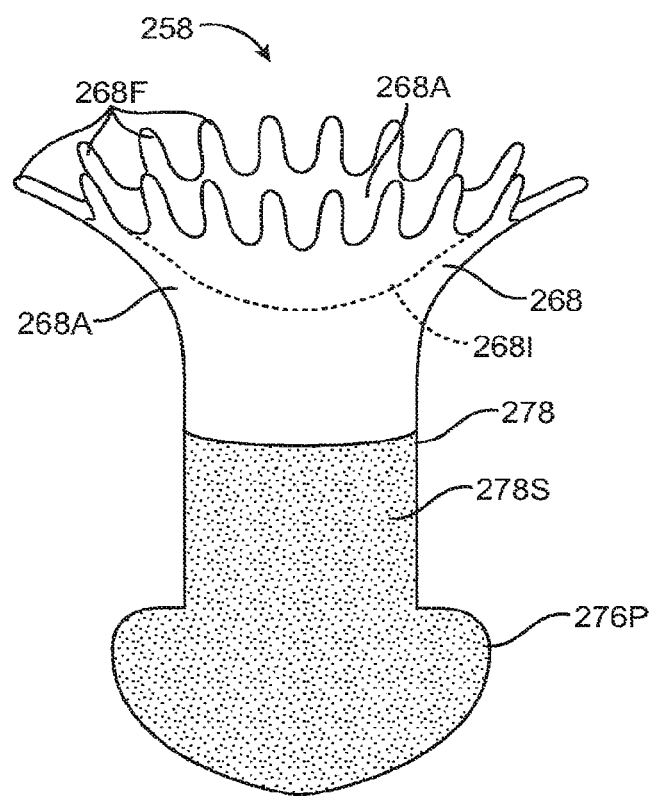
FIG. 2J shows a side view of a sustained release implant with a core comprising an exposed surface area with several soft brush-like members extending therefrom, according to an embodiment of the present invention.

FIG. 2J shows a side view of a sustained release implant 258 with a core 268 comprising an exposed surface area with several soft brush-like members 268F, according to an embodiment of the present invention. Drug core 268 is partially covered with a sheath body 278 that extends at least partially over drug core 268 to define exposed surface 268A. Sheath body 278 comprises a shaft portion 278S. Soft brush-like members 268F extend outward from drug core 268 and provide an increased exposed surface area to drug core 268. Soft brush-like members 268F are also soft and resilient and easily deflected such that these members do not cause irritation to neighboring tissue. Although drug core 268 can be made of many materials as explained above, silicone is a suitable material for the manufacture of drug core 268 comprises soft brush like members 268F. Exposed surface 268A of drug core 268 also includes an indentation 268I such that at least a portion of exposed surface 268A is concave.

Figure 2K:
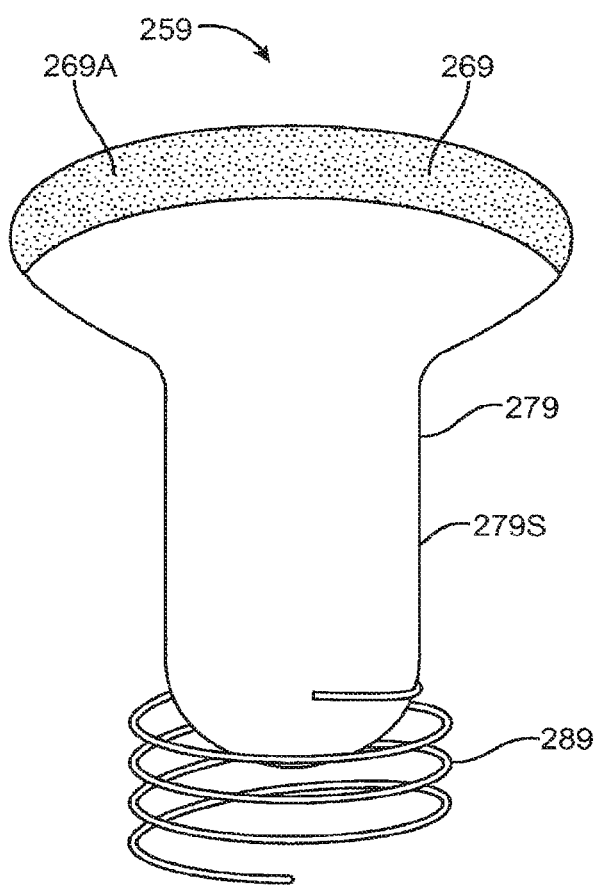
FIG. 2K shows a side view of a sustained release implant with a drug core comprising a convex exposed surface and a retention structure, according to an embodiment of the present invention.

FIG. 2K shows a side view of a sustained release implant 259 with a drug core 269 comprising a convex exposed surface 269A, according to an embodiment of the present invention. Drug core 269 is partially covered with a sheath body 279 that extends at least partially over drug core 269 to define convex exposed surface 269A. Sheath body 279 comprises a shaft portion 279S. Convex exposed surface 269 provides an increased exposed surface area above the sheath body. A cross sectional area of convex exposed surface 269A is larger than a cross sectional area of shaft portion 279S of sheath body 279. In addition to the larger cross sectional area, convex exposed surface 269A has a larger surface area due to the convex shape that extends outward on the core. A retention structure 289 can be attached to sheath body 279. Retention structure 289 can comprise any of the retention structures as describe herein, for example a coil comprising a super elastic shape memory alloy such as Nitinol™. Retention structure 289 can be dip coated to make retention structure 289 biocompatible.

Figure 2L:
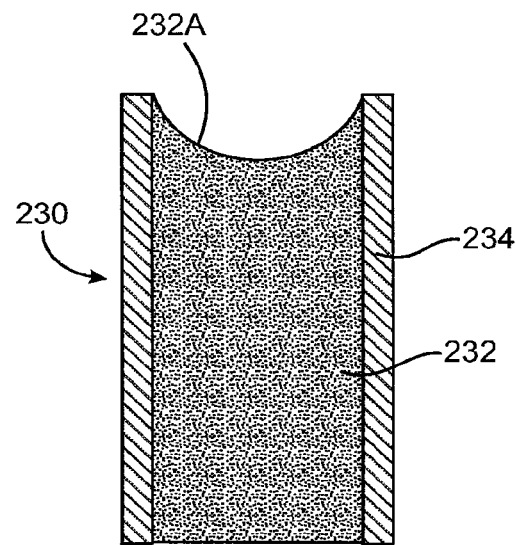
FIG. 2L shows a side view of a sustained release implant with a drug core comprising a concave indented surface to increase exposed surface area of the core, according to an embodiment of the present invention.

FIG. 2L shows a side view of a sustained release implant 230 with a drug core 232 comprising a concave indented surface 232A to increase exposed surface area of the core, according to an embodiment of the present invention. A sheath body 234 extends at least partially over drug core 232. Concave indented surface 232A is formed on an exposed end of drug core 232 to provide an increased exposed surface area of the drug core.

Figure 2M:
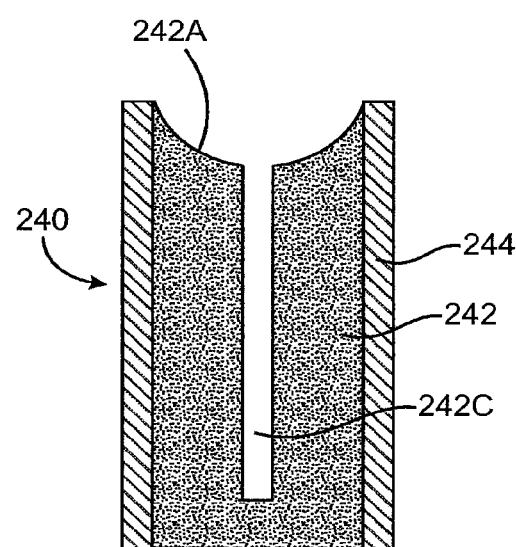
FIG. 2M shows a side view of a sustained release implant with a drug core comprising a concave surface with a channel formed therein to increase an exposed surface area of the core, according to an embodiment of the present invention.

FIG. 2M shows a side view of a sustained release implant 240 with a drug core 242 comprising a concave surface 242A with a channel 242C formed therein to increase an exposed surface area of the core, according to an embodiment of the present invention. A sheath body 244 extends at least partially over drug core 242. Concave indented surface 242A is formed on an exposed end of drug core 232 to provide an increased exposed surface area of the drug core. Channel 242C formed in drug core 242 to provide an increased exposed surface area of the drug core. Channel 242C can extend to concave indented surface 242A such that channel 242C and provide an increase in surface area of the core exposed to the tear or tear film.

Figure 3A:
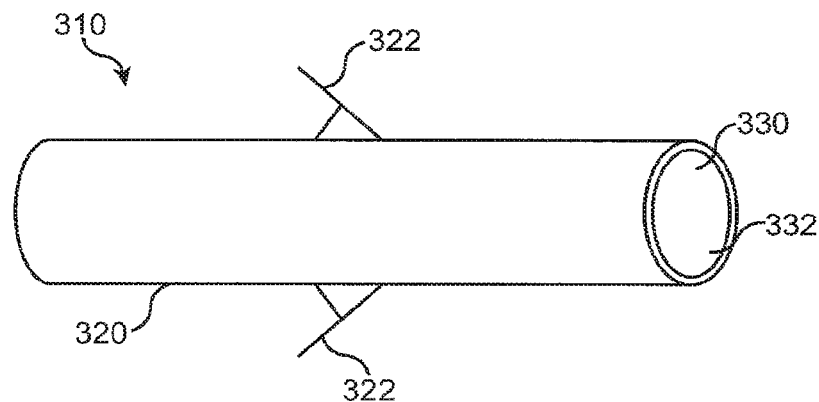
FIG. 3A shows an implant with a sheath body with extensions that attach the sheath body and core to the retention element, according to an embodiment of the present invention.

FIG. 3A shows an implant 310 comprising a sheath body 320 with extensions 322, according to an embodiment of the present invention. Extensions 322 attach sheath body 320 to the retention element to retain the core near the punctum. Sheath body 320 extends over core 330 to define an exposed surface 332 of core 330. Extensions 322 can be resilient and engage the retention element and/or occlusive element to attach the sheath body core to the retention element to retain the core near the punctum.

Figure 3B:
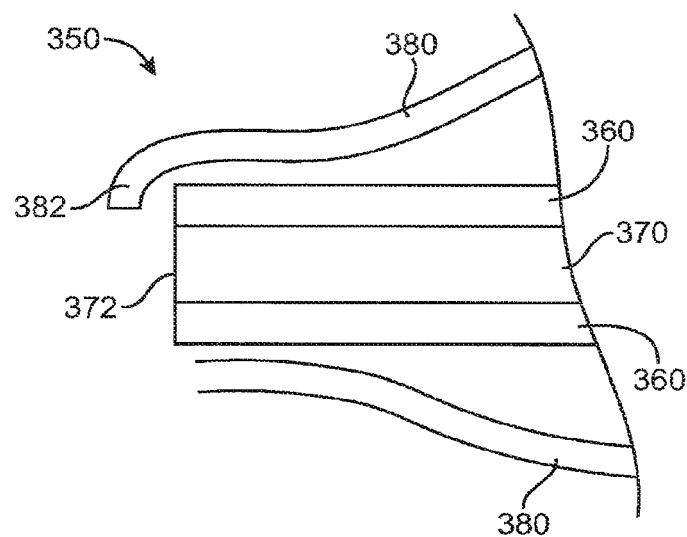
FIG. 3B shows an implant with a retention element with an extension that retains a sheath body and a core, according to an embodiment of the present invention.

FIG. 3B shows an implant 350 comprising a retention element 380 with an extension 382, according to an embodiment of the present invention. Extension 382 retains a sheath body 360 and a core 370. Sheath body 360 extends over core 370 to define an exposed surface 372 of core 370. Exposed surface 372 is disposed near the proximal end of core 370. Extension 382 extends downward to retain core 370 and sheath body 370.

Figure 4A:
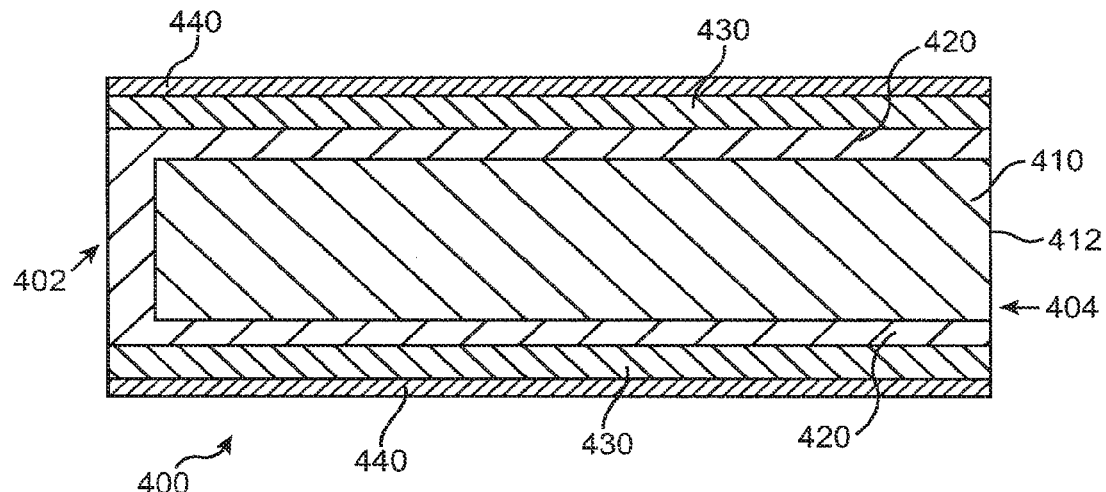
FIGS. 4A and 4B show a cross-sectional view of an implant with a retention structure that is shorter in length while in a large cross-sectional profile configuration than a small cross-sectional profile configuration, according to an embodiment of the present invention.
Figure 4B:
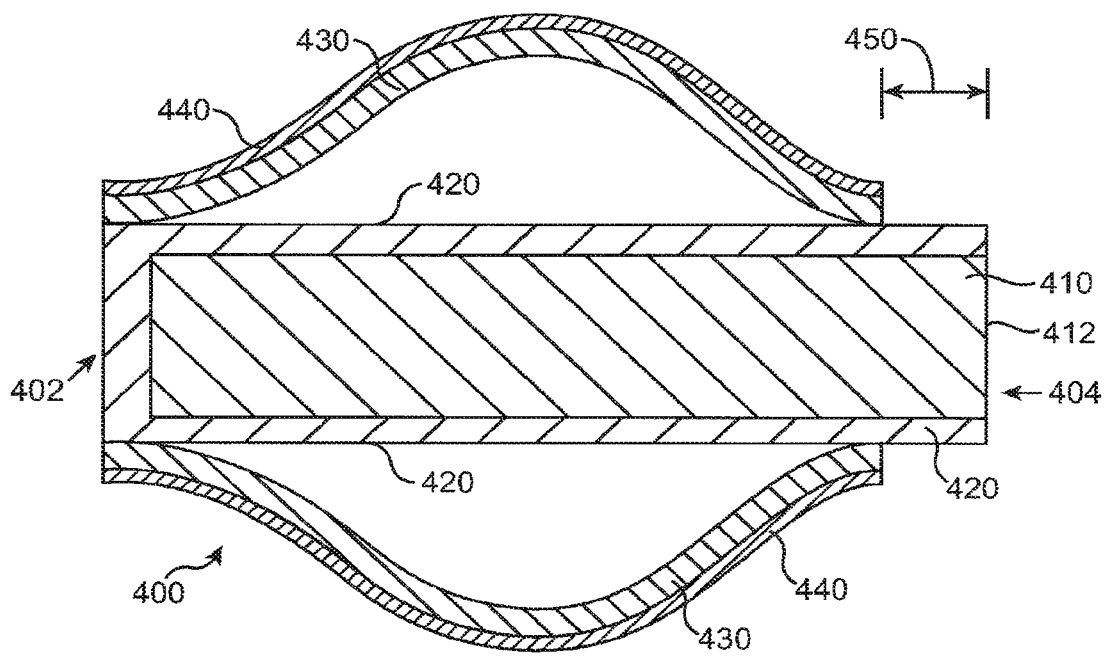

FIGS. 4A and 4B show a cross-sectional view of an implant 400 with a retention structure 430 that is shorter in length while in a large cross-sectional profile configuration than a small cross-sectional profile configuration, according to an embodiment of the present invention. Implant 400 includes a distal end 402 and a proximal end 404. Implant 400 includes a drug core 410 and a sheath body 420. Sheath body 420 at least partially covers drug core 410 and defines an exposed surface 412 of drug core 410. An occlusive element 440 can be attached to and supported by retention structure 430. Occlusive element 440 can move with retention structure 430, for example when retention element 430 expands from a small profile configuration to a large profile configuration. In many embodiments, the retention structure and occlusive element are sized to correspond to a diameter of the canaliculus, for example to match a diameter of the 18 canaliculus or slightly larger than the canalicular diameter, so as occlude fluid flow through the canaliculus and/or anchor in the canaliculus.

As shown in FIG. 4A, retention structure 430 and occlusive element 440 are in a small profile configuration. Such a small profile configuration can occur while the occlusive element and retention structure are placed in a tip of an insertion tool and covered for deployment. Retention element 430 and occlusive element 440 extend fully along the length of sheath body 420 and drug core 410. Retention element 430 is attached to sheath body 420 near distal end 402. In many embodiments, retention structure 430 and occlusive element 440 have diameters that are sized to fit inside and slide within the canaliculus while in the small profile configuration, and the retention structure and occlusive element can be sized to anchor within the canaliculus while in a second large profile configuration.

As shown in FIG. 4B, retention structure 430 and occlusive element 440 are in a large profile configuration. Such a large profile configuration can occur when the occlusive element and retention structure are placed in the canaliculus. In the large profile configuration, the length of occlusive element 440 and retention structure 430 is shorter than in the small profile configuration by a distance 450. The proximal end of retention structure 430 and occlusive element 440 can slide over sheath body 420 when the sheath body and retention structure assume the large profile configuration such that the proximal end of drug core 410 and sheath body 420 extend from the retention structure and occlusive element. In some embodiments, the sheath body is shorter than drug core 410 by distance 450 so that more of the drug core is exposed while the retention structure and occlusive element are in the large profile configuration than is exposed while the retention structure and occlusive element are in the small profile configuration. In such embodiments, the retention structure and occlusive element retract to expose the drug core.

Figure 5A:
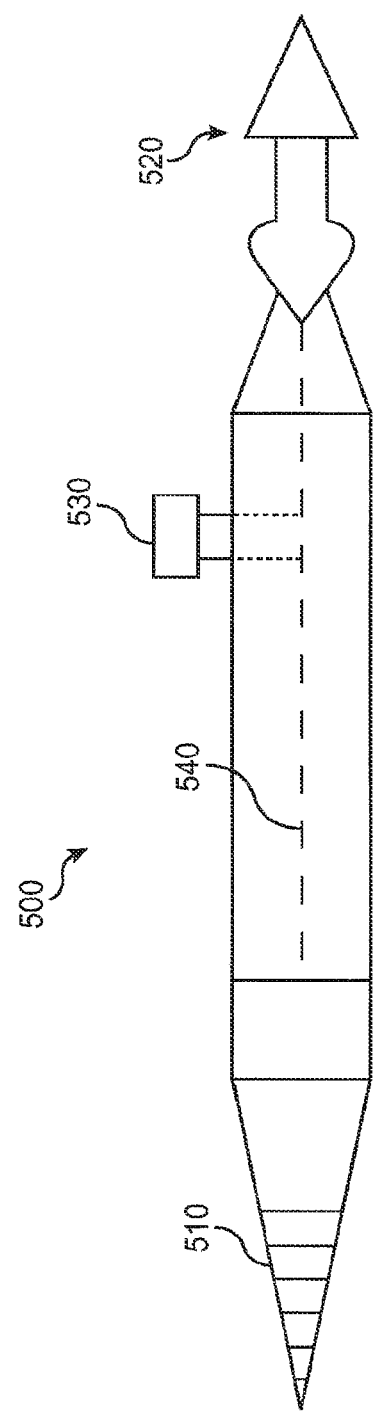
FIG. 5A shows an insertion tool to insert an implant into the punctum with a plunger that can be depressed, according to an embodiment of the present invention.
Figure 5B:
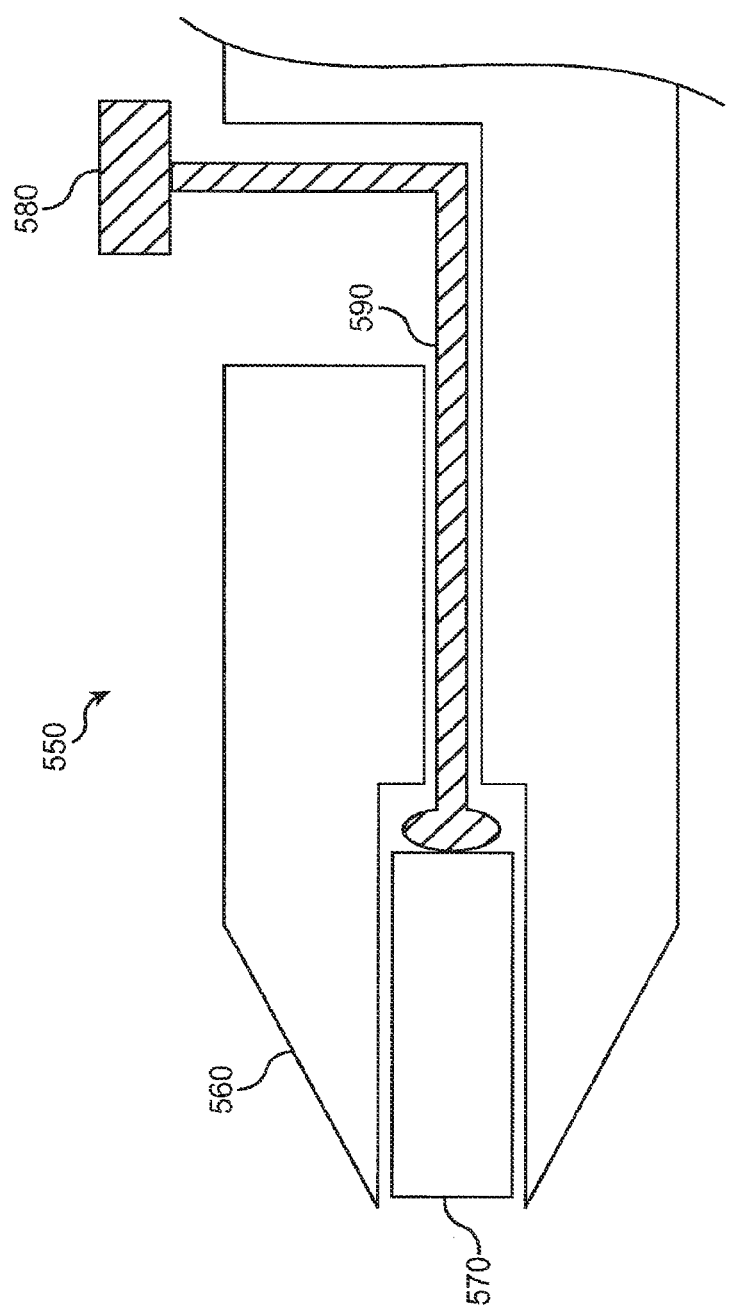
FIG. 5B shows an insertion tool to insert an implant into the punctum with a plunger that can slide, according to an embodiment of the present invention.
Figure 6:
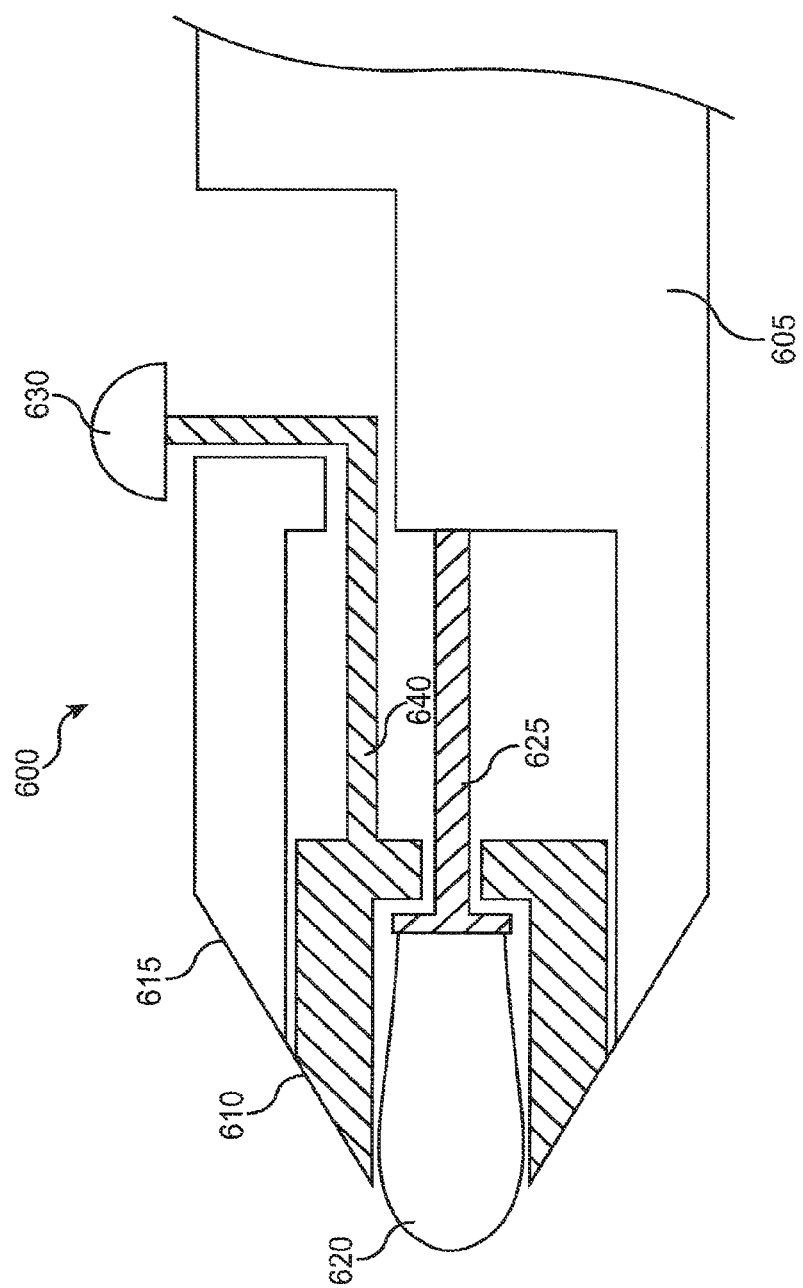
FIG. 6 shows an insertion tool to insert an implant into the punctum with a sheath that retracts proximally, according to an embodiment of the present invention.

FIGS. 5A to 6 show embodiments of tools that can be used to insert many of the implants as describe herein.

FIG. 5A shows an insertion tool 500 to insert an implant into the punctum with a plunger 530 that can be depressed, according to an embodiment of the present invention. Insertion tool 500 includes a dilator 510 that can be inserted into the punctum to pre-dilate the punctum prior to insertion of an implant. An implant 520 can be pre-loaded onto tool 500 prior to dilation of the punctum. An internal wire 540 can be connected to implant 520 to retain the implant. Following pre-dilation of the punctum with dilator 510, tool 500 can be used to insert implant 520 into the punctum. While implant 520 is positioned in the punctum, plunger 530 can be depressed to engage wire 540 and release implant 520 from tool 500. In some embodiments, wire 540 may comprise a sharpened needle tip that penetrates implant 520. Implant 520 may comprise a drug core with a resilient material, for example silicone, such that the drug core material contracts when the needle is removed.

FIG. 5B shows an insertion tool 550 to insert an implant 570 into the punctum with a plunger that can slide, according to an embodiment of the present invention. Insertion tool 550 includes a dilator 560 with a conical section to dilate the punctum. Implant 550 includes a plunger 580 that can slide distally to advance implant 570 into the lumen. A shaft 590 is connected to plunger 580 to advance implant 570 distally when plunger 580 is advanced distally. While the punctum is dilated with dilator 560, plunger 580 can be advanced distally to place implant 570 in the canalicular lumen near the punctum. In many embodiments, a button can be depressed to advance distally the implant into the lumen, for example a button connected to shaft 590 with an intermediate mechanism.

FIG. 6 shows an insertion tool 600 to insert an implant into the punctum with a sheath 610 that retracts to position the implant in the canalicular lumen, according to an embodiment of the present invention. At least a portion of sheath 610 is shaped to dilate the punctum. Sheath 610 is shaped to hold an implant 620 in a small profile configuration. Insertion tool 600 includes an annular structure 615, which can comprise a portion of a body 605 of insertion tool 600. Sheath 610 and annular structure 615 are shaped to dilate the punctum and often comprise proximally inclined surfaces to dilate the punctum. Implant 620, sheath 610 and annular structure 615 can be at least partially inserted into the punctum to place the implant in the canalicular lumen. Annular structure 615 is disposed over sheath 610 so that sheath 610 can be retracted and slide under annular structure 615. A stop 625 can be connected to body 605 to retain implant 620 at the desired depth within the canalicular lumen while sheath 610 is retracted proximally to expose implant 620.

Once implant 620 has been positioned in the canalicular lumen at the desired depth in relation to the punctum, sheath 610 is retracted to expose implant 620 at the desired location in the canalicular lumen. A plunger 630 can be used to retract sheath 610. A shaft 640 mechanically couples sheath 610 to plunger 630. Thus, retraction of plunger 630 in the proximal direction can retract sheath 610 in the proximal direction to expose implant 620 at the desired location in the canalicular lumen. Implant 620 can be any of the implants as described herein. Often, implant 620 will comprise a resilient member that expands to a large profile configuration when sheath 610 is retracted. In many embodiments, insertion tool 600 can include a dilator to dilate the punctum prior to insertion of the implant, and the dilator can be positioned on an end of the insertion tool that opposes the end loaded with the implant, as described herein above.

Figure 7A:
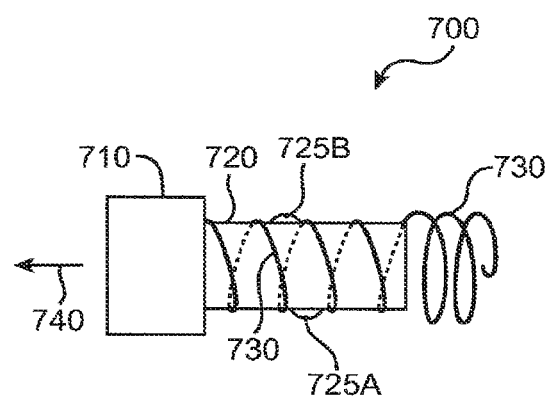
FIGS. 7A to 7C schematically illustrate replacement of a drug core and a sheath body, according to an embodiment of the present invention.
Figure 7B:
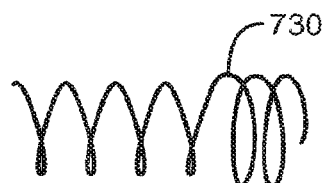
Figure 7C:
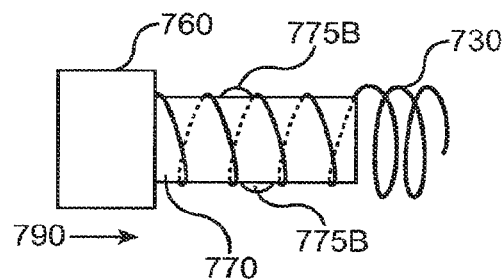

FIGS. 7A to 7C schematically illustrate replacement of a drug core 710 and a sheath body 720, according to an embodiment of the present invention. An implant 700 comprises drug core 710, sheath body 720 and a retention structure 730. Implant 700 can include an occlusive element support by and movable with retention structure 730. Often retention structure 730 can assume a first small profile configuration prior to implantation and a second large profile configuration while implanted. Retention structure 730 is shown in the large profile configuration and implanted in the canalicular lumen. Sheath body 720 includes extension 725A and extension 725B to attach the sheath body and drug core to retention structure 730 so that the sheath body and drug core are retained by retention structure 730. Drug core 710 and sheath body 720 can be removed together by drawing drug core 710 proximally as shown by arrow 730. Retention structure 730 can remain implanted in the canalicular tissue after drug core 710 and sheath body 720 have been removed as shown in FIG. 7B. A replacement core 760 and replacement sheath body 770 can be inserted together as shown in FIG. 7C. Such replacement can be desirable after drug core 710 has released effective amounts of therapeutic agent such that the supply of therapeutic agent in the drug core has diminished and the rate of therapeutic agent released is near the minimum effective level. Replacement sheath body 770 includes extension 775A and extension 775B. Replacement drug core 760 and replacement sheath body 770 can be advanced distally as shown by arrow 790 to insert replacement drug core 760 and replacement sheath body 770 into retention structure 730. Retention structure 730 remains at substantially the same location while replacement drug core 760 and replacement sheath body 770 are inserted into resilient member 730.

Figure 8A:
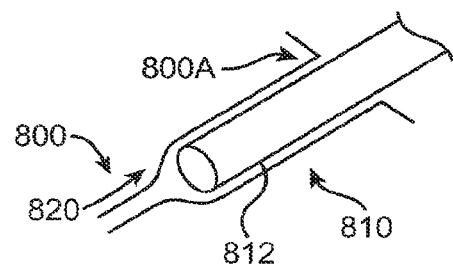
FIGS. 8A to 8C show deployment of a sustained release implant, according to an embodiment of the present invention.
Figure 8B:
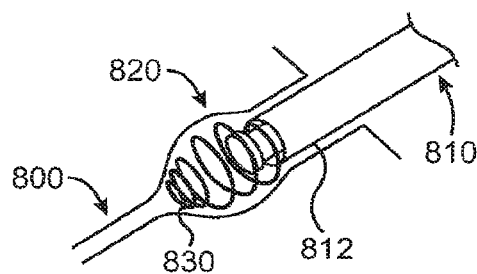
Figure 8C:
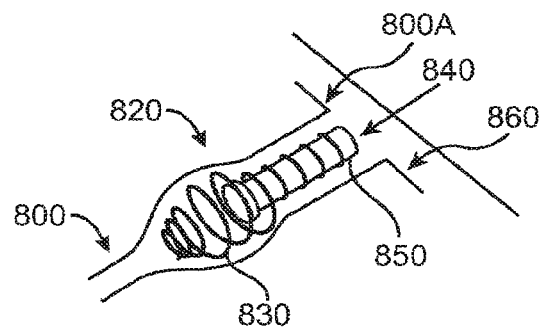

FIGS. 8A to 8C show deployment of a sustained release implant, according to an embodiment of the present invention. As shown in FIG. 8A, a deployment instrument 810 is inserted into a canaliculus 800 through a punctum 800A. A sustained release implant 820 is loaded into a tip of deployment instrument 810, and a sheath 812 covers sustained release implant 820. Retention structure 830 assumes a small profile configuration while sheath 812 is positioned over retention structure 830. As shown in FIG. 8B, outer sheath 812 of deployment instrument 810 is withdrawn to expose a retention structure 830 of sustained release implant 820. The exposed portion of retention element 830 assumes a large profile configuration. As shown in FIG. 8C, deployment instrument 810 has been removed and sustained release implant 820 is implanted in canaliculus 800. A drug core 840 is attached retention structure 830 and retained in the canaliculus. An outer body sheath 850 covers at least a portion of drug core 840 and drug core 840 releases a therapeutic agent into a liquid tear or tear film 860 near punctum 800A of canaliculus 800.

Figure 9A:
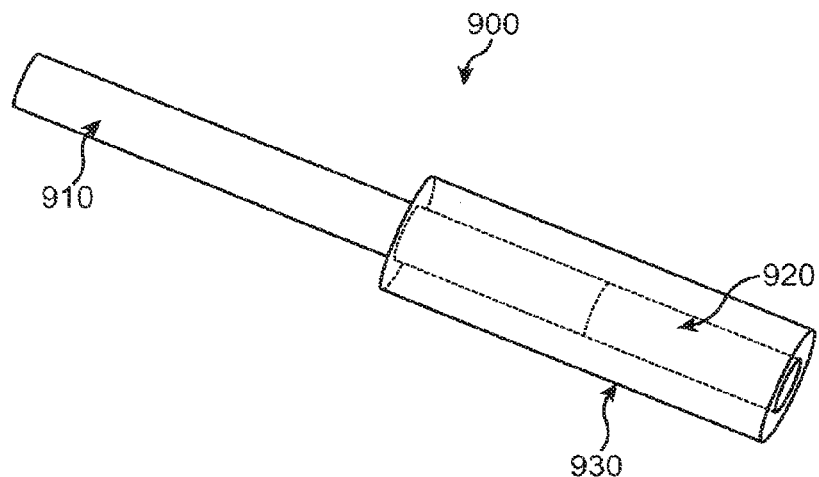
FIG. 9A shows a drug delivery system with a sleeve to hold the drug core and a hydrogel retention element, according to embodiments of the present invention.

FIG. 9A shows a drug delivery system 900 with a sleeve 930 to hold a drug core 920 and a hydrogel retention element 910, according to embodiments of the present invention. In many embodiments, the collar comprises silicone. The drug core comprises matrix with a therapeutic agent and can have a sheath as described above. Hydrogel retention element 910 can be placed inside sleeve 930, and when placed in the punctum, the hydrogel retention element 910 expands as it absorbs fluid. The retention element can comprise many materials that swell. The sleeve acts holds the drug core insert and the hydrogel rod together and prevents the hydrogel member from becoming dislodged from the assembled drug delivery system. As the hydrogel expands the silicone collar gives slightly to allow expansion and at the same time forms a tighter restriction around the hydrogel element so as to prevent movement of the hydrogel out of the sleeve. In FIG. 9A, the drug delivery system is shown with the hydrogel retention element in the pre-insertion configuration with a slender profile for insertion through the punctum into the canaliculus. The hydrogel is not substantially hydrated in the narrow profile configuration and has a water content of less than about 10%, for example 1%.

Figure 9B:
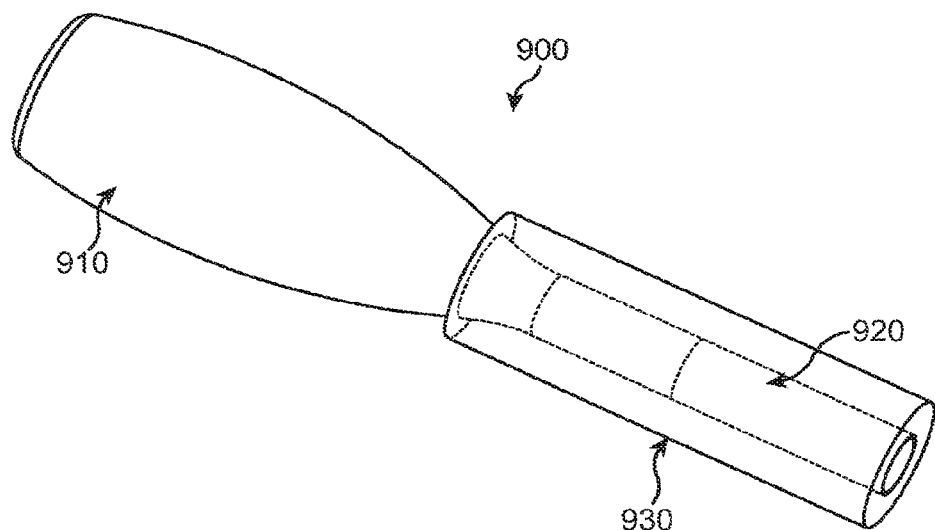
FIG. 9B shows a drug delivery system as in FIG. 9A with a hydrated hydrogel retention element, according to embodiments of the present invention.

FIG. 9B shows drug delivery system 900 as in FIG. 9A with hydrogel retention element 910 hydrated, according to embodiments of the present invention. In the inserted configuration the hydrogel is hydrated and expanded in the canaliculus. This expansion can tightly fit many sizes of patients due to the broad range of expansion of the hydrogel. In many embodiments, the silicone sleeve can take additional forms to help with positioning in the punctum. In the expanded configuration, the hydrogel can assume an equilibrium concentration of water, for example from about 50% to 95% water.

Figure 9C:
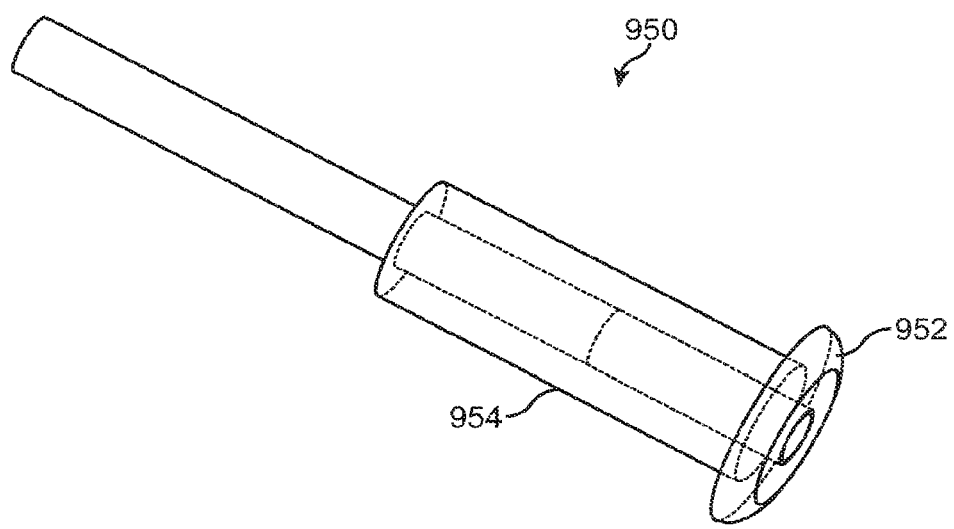
FIG. 9C shows a drug delivery system as in FIG. 9A with a sleeve comprising a silicone collar to rest on the exterior of the punctum, according to embodiments of the present invention.

FIG. 9C shows a drug delivery system 950 as in FIG. 9A with a sleeve 954 comprising a silicone collar 952 to rest on the exterior of the punctum, according to embodiments of the present invention. The collar can be sized such that the device does not engage too deeply into the punctum. For example, the collar can rest on the exterior of the punctum.

Figure 9D:
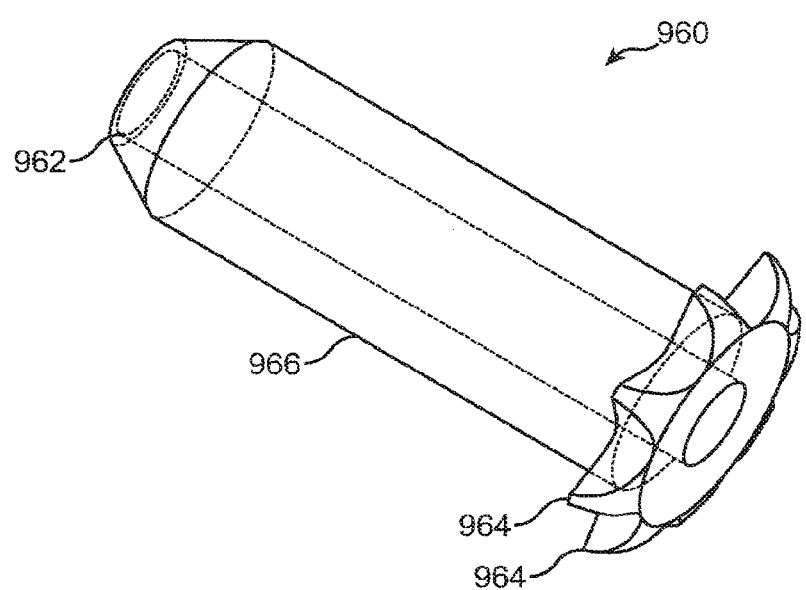
FIG. 9D shows sleeve a drug delivery system with a taper on the distal canalicular end of the sleeve to assist with insertion into the punctum and flanges to rest on the exterior of the punctum, according to embodiments of the present invention.

FIG. 9D shows a sleeve 966 of a drug delivery system 960 with a taper 962 on the distal canalicular end of the sleeve to assist with insertion into the punctum and flanges 964 to rest on the exterior of the punctum, according to embodiments of the present invention. The sleeve can comprise many flanges for example 2 flanges, 4 flanges, 8 flanges or 16 flanges that can be sized to rest of the exterior of the punctum.

Figure 9E:
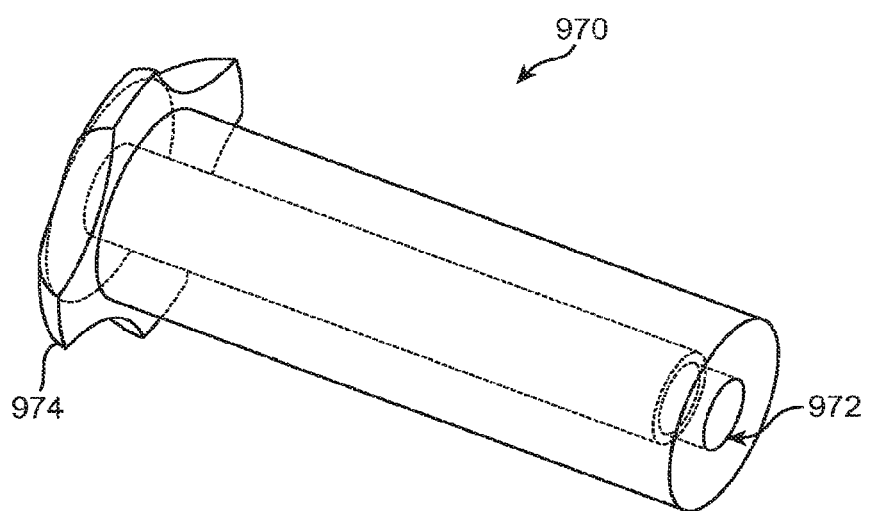
FIG. 9E shows a sleeve of a drug delivery system with a restriction on the distal canalicular end of the sleeve to retain the hydrogel retention element in the sleeve, according to embodiments of the present invention.

FIG. 9E shows a sleeve 974 of a drug delivery system 970 with a restriction 972 on the distal canalicular end of the sleeve to retain the hydrogel retention element in the sleeve, according to embodiments of the present invention. Restriction 972 comprises a flange to engage the hydrogel when the hydrogel expands. Restriction 972 can also be formed with tabs spike and other protrusions to engage the hydrogel as the hydrogel urges radially outward from an axis of the hydrogel retention element.

Figure 9F:
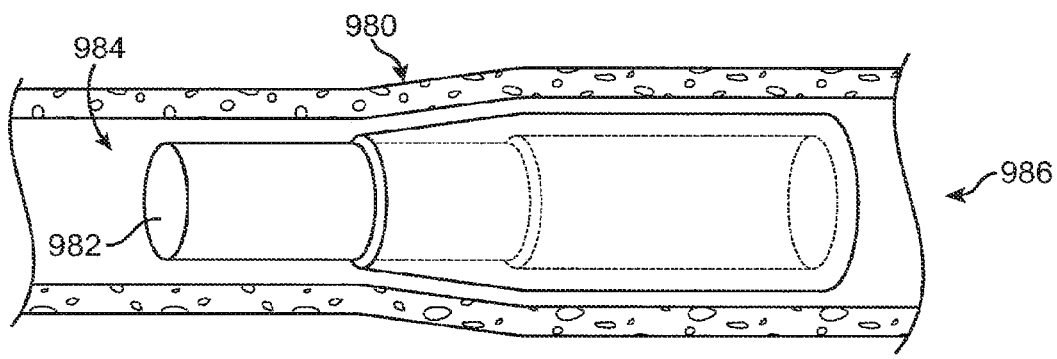
FIG. 9F shows the drug delivery system with a hydrogel retention element during insertion into the canalicular lumen, according to embodiments of the present invention.

FIG. 9F shows a drug delivery system 980 with a hydrogel retention element 982 during insertion into a canalicular lumen 984, according to embodiments of the present invention. The retention element is inserted through a punctal opening 986 in a narrow profile configuration. The retention element comprises substantially dry hydrogel in the narrow profile configuration. In many embodiments, drug delivery system comprises flanges on an end of the sleeve opposite the retention element, as described above, such that the flanges rest on the exterior of the punctum while the retention element is expanded in the canalicular lumen.

Figure 9G:
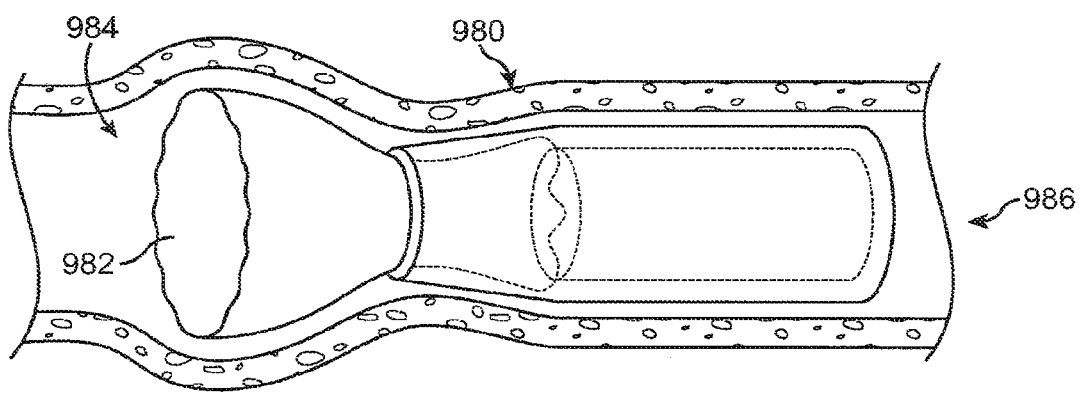
FIG. 9G shows a drug delivery system as in FIG. 9F with an expanded hydrogel retention element following insertion into the canalicular lumen, according to embodiments of the present invention.

FIG. 9G shows drug delivery system 980 as in FIG. 9F with hydrogel retention element 982 expanded following insertion into the canalicular lumen, according to embodiments of the present invention. The hydrogel retention element is expanded to engage the sleeve and has caused a slight elastic deformation of the resilient silicone sleeve. The hydrogel retention element urges outward with sufficient force to cause slight deformation of the wall of the canalicular lumen 984.

In many embodiments, the drug delivery system comprises a modular system that includes a drug insert and a commercially available punctum plug that can accommodate the drug insert. The drug insert can be adapted to be placed in the bore of the punctum plug, and can be held in place via an interference fit between the outer diameter of the drug insert and the inner diameter of the silicone plug bore. The assembled system can be packaged and sterilized and delivered to the physician in this configuration.

In many embodiments, a punctal plug for treating dry eye comprises a swellable material connected to a sleeve body without a drug core, for example many of the swellable materials and sleeve bodies described in FIGS. 9A to 9G. In some embodiments, dry eye can be treated with many of the punctal plugs as described herein in which the core does not include a therapeutic agent comprised therein. In many embodiments the tube body is sized to occlude the punctum to treat dry eye. In some embodiments, the body may be smaller than the punctum such that the swollen hydrogel can occlude the punctum. The body can comprises a protrusion comprising a flange, rim, wing or the like that is sized to remain on the exterior of the punctum while the body is positioned in the punctum so as to facilitate removal of the plug body and retention structure from the punctum while the hydrogel retention element is swollen. Work in relation to the present invention suggests that current punctal plugs comprising hydrogel may be difficult to remove as the hydrogel may tear, and the structures described herein to retain hydrogel with a body can facilitate removal of the swollen hydrogel retention element.

FIG. 10A shows a drug core insert 1010 for use with a punctal plug, according to embodiments of the present invention. Drug core insert can comprise a drug sheath 1014 comprising polyimide and/or many of the materials that are substantially impermeable to the therapeutic agent as described above. The drug core comprise many of the shapes described above, for example a cylindrical rod. A cyanoacrylate film can be applied to one end of the drug core insert. An opposing end of the drug core insert is exposed to permit diffusion of the therapeutic agent into the tear of the eye as described above. In a specific embodiment, the drug core insert comprises a cross sectional size, for example a diameter, of about 0.3 mm. A length of the drug core insert is about 0.9 mm.

The drug insert may comprise a thin-walled polyimide tube with a drug core comprising Latanoprost dispersed in Nusil 6385 (MAF 970), a medical grade solid silicone that serves as the matrix for drug delivery. The distal end of the drug insert can be sealed with a cured film of solid Loctite 4305 medical grade adhesive. Since the drug insert can be placed within the bore of the punctum plug, the Loctite 4305 adhesive may not come into contact with either tissue or the tear film. The inner diameter of the drug insert can be 0.32 mm; the length can be 0.95 mm. In three embodiments, the Latanoprost concentration can be tested clinically: Drug core containing 3.5, 7 or 14 µg Latanoprost. In many embodiments, an overall elution rate can be approximately 100 ng/day, and the drug core can comprise 14 µg of Latanoprost, such that the drug can be delivered for ~120 days. The overall weight of the drug core, including Latanoprost, can be approximately 70 µg. The weight of the drug insert including the polyimide sleeve can be approximately 100 µg.

All materials currently being used in the construction of the drug insert are medical grade materials that have passed a battery of safety/toxicity tests. The table below summarizes the biocompatibility testing performed by the manufacturers on the drug insert materials.

In many embodiments, the drug core can comprise silicone. Latanoprost, at the desired concentration, can be dispersed in uncured Nusil 6385 silicone, injected into a polyimide sleeve, and cured at room temperature. This method can result in a solid silicone matrix comprising the desired concentration of Latanoprost.

In many embodiments, the sleeve can comprise polyimide. The polyimide sleeve can house the drug core so as to provide structural support and a barrier to lateral drug diffusion. The inner diameter of the sleeve can be 0.32 mm, and the wall thickness can be 0.013 mm.

FIG. 10B shows a punctal plug 1020 comprising an internal cavity 1022 with a cylindrical shape, according to embodiments of the present invention. Cavity 1022 is sized to 10 receive drug core insert 1010 with a friction fit. Punctal plug 1020 can comprise many commercially available punctal plugs, for example the Medtronic Tear Pool Punctal Plug, the "Parasol Punctal Occluder System" available from Odyssey of Memphis, TN, and/or the Eagle Vision Plug available from Eagle Vision of Memphis, TN In some embodiments, the punctal plug comprises a custom punctal plug, for example sized custom plugs that are selected in response to patient measurements. In many embodiments, the punctal plug has a length of about 2 mm and a width of about 1 mm.

FIG. 10C shows a punctal plug as in FIG. 10B with a drug core as in FIG. 10A inserted therein, according to embodiments of the present invention. In many embodiments, insertion and removal of the drug delivery system can accomplished in a similar manner as for other commercially available punctum plugs. The plug can be inserted into the punctum using forceps or an insertion tool, for example a tool as shown above with a needle sized for insertion into the core. When placed in the superior (or inferior) punctum of the eye, the proximal end of the drug core is exposed to the tear fluid. As the tears come in contact with the exposed proximal surface of the drug core, the therapeutic agent, for example Latanoprost, is slowly eluted. The drug delivery system may be removed using forceps.

Figure 11:
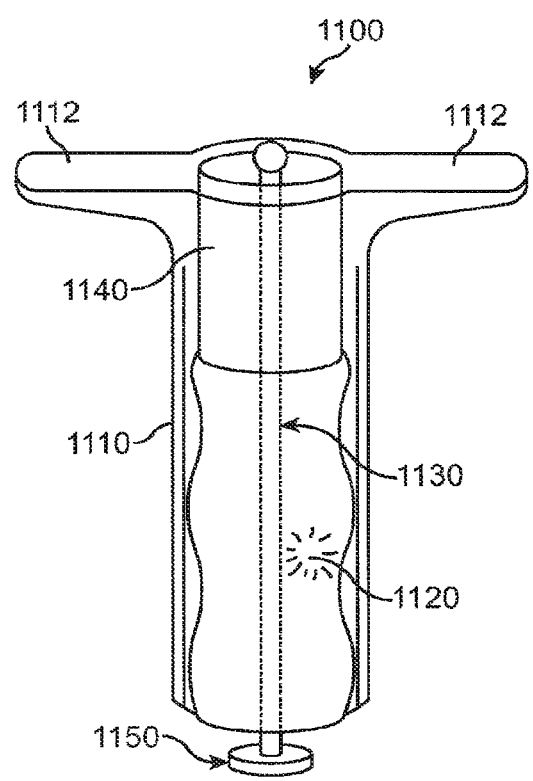
FIG. 11 shows a punctal plug drug delivery system comprising a drug core, and a retention structure that includes a sleeve with wings formed thereon, according to embodiments of the present invention.

FIG. 11 shows a punctal plug drug delivery system 1100 comprising a drug core 1140, and a retention structure that includes a sleeve 1110 with wings 1112 formed thereon, according to embodiments of the present invention. In many embodiments, the retention structure also comprises a hydrogel retention element 1120. Wings 1112 can limit penetration of the device into the punctum such that the wings rest on the exterior of the punctum while device is retained with hydrogel retention element 1120 in the canalicular lumen. In many embodiments, wings 1112 prevent the proximal end of the plug from migrating distally into the canalicular lumen. Wings 1112 may aid in removal of the device. A 1150 cap can be included near the distal end of the device to limit distal expansion of the hydrogel. A suture 1130 can extend from the proximal end to the distal end to hold the drug core and hydrogel retention element inside sleeve 1110.

Figure 12B:
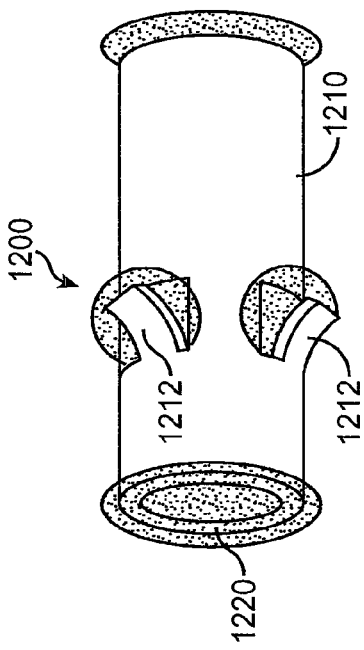
FIG. 12B shows a retention structure as in FIG. 12A with the tabs urged radially outward in response to hydration of the hydrogel material, according to embodiments of the present invention.
Figure 12A:
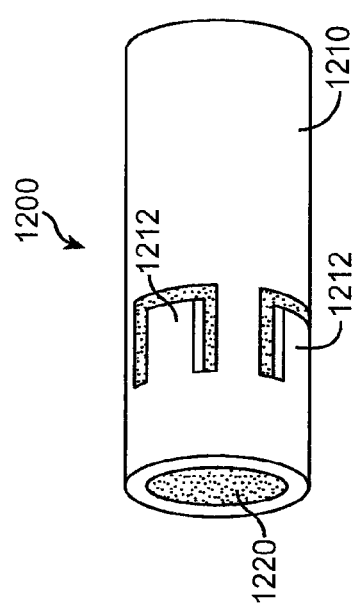
FIG. 12A shows a retention structure comprising a sleeve with tabs and hydrogel, according to embodiments of the present invention.

FIG. 12A shows a retention structure 1200 comprising a sleeve 1210 with tabs 1212 and hydrogel 1220, according to embodiments of the present invention. Retention structure 1200 can be combined with many of the drug cores described above. Sleeve 1210 comprises an annular shell that covers hydrogel 1220. Hydrogel 1220 can have a cylindrical shape to fit inside sleeve 1210. While hydrogel 1220 is dry, retention structure 1200 remains in a narrow profile configuration. Tabs 1212 define an opening in sleeve 1210 that permits water to enter hydrogel 1220 when sleeve 1210 is inserted into the punctum. In some embodiments, the sleeve may also comprise a hydrogel component added to the silicone of the sleeve so that the sleeve also expands to increase retention.

FIG. 12B shows a retention structure 1200 as in FIG. 12A with tabs 1212 urged radially outward in response to hydration of the hydrogel material, according to embodiments of the present invention. When water enters the opening in sleeve 1210, hydrogel 1220 expands to urge tabs 1212 radially outward. The retention structure can engage the luminal wall to retain the drug elution device in the canaliculus. As the hydrogel urges outward, the hydrogel expands into the openings near the tabs such that the hydrogel is retained in the sleeve.

Figure 12D:
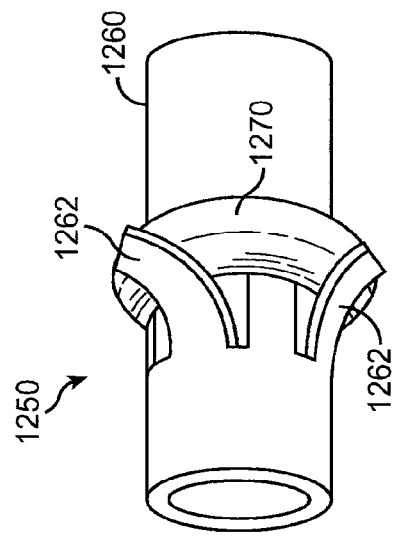
FIG. 12D shows a retention structure as in 12C comprising a sleeve with tabs and an annular hydrogel expansion member, according to embodiments of the present invention.
Figure 12C:
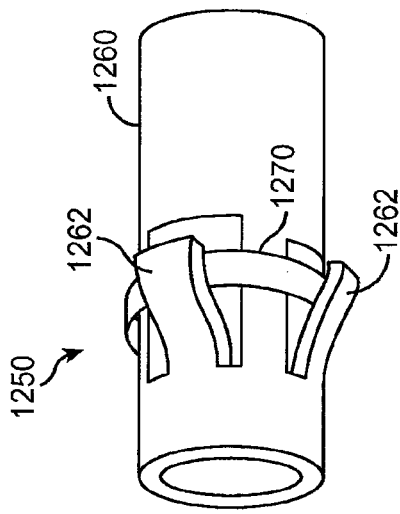
FIG. 12C shows a retention structure comprising a sleeve with tabs and an annular hydrogel expansion member, according to embodiments of the present invention.

FIG. 12C shows a retention structure 1250 comprising a sleeve 1260 with tabs 1262 and an annular hydrogel expansion member 1270, according to embodiments of the present invention. While structure 1250 remains dry, the structure retains a narrow profile configuration. The drug core can be comprised within the annular sleeve as described above.

FIG. 12D shows a retention structure as in 12C comprising a sleeve with tabs and an annular hydrogel expansion member, according to embodiments of the present invention. Upon hydration of annular hydrogel expansion member 1270, the annular hydrogel expansion member urges outward against tabs 1262 to push the tabs outward against the luminal wall.

Figure 13:
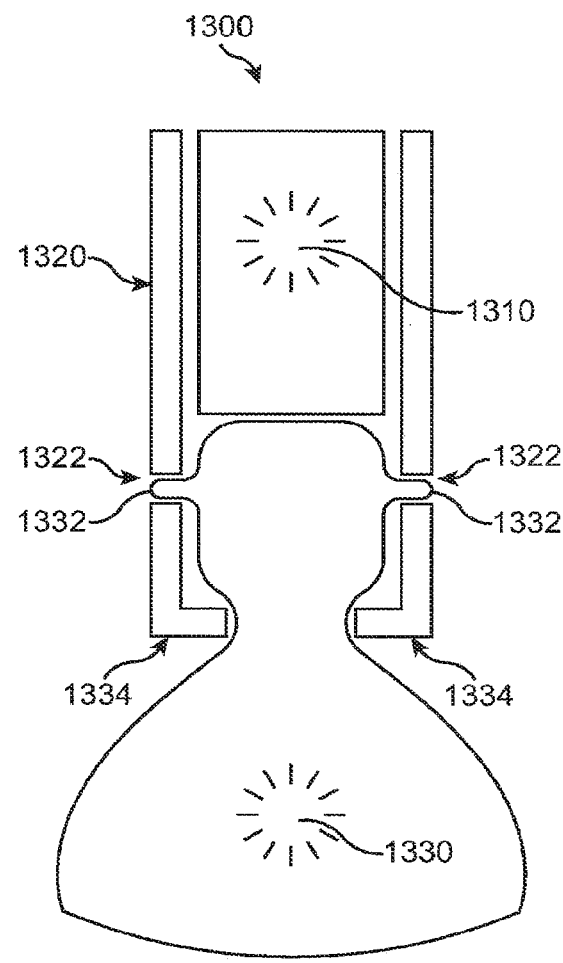
FIG. 13 shows drug delivery device with a hydrogel retention structure comprising a sleeve with cross holes and lock tabs and/or flanges to hold the hydrogel in place upon expansion of the hydrogel, according to embodiments of the present invention.

FIG. 13 shows a drug delivery device 1300 with a retention structure comprising a hydrogel retention element 1330, a sleeve 1320 with cross holes 1322 therein and lock tabs 1334 and/or flanges to hold the hydrogel in place upon expansion of the hydrogel, according to embodiments of the present invention. Drug delivery device 1300 comprises a drug core insert 1310 as described above. Cross holes 1322 permit water to pass and hydrate hydrogel retention element 1330. Expansion of hydrogel retention element 1330 urges some of the hydrogel against sleeve 1320 and through cross holes 1322 such that the hydrogel retention element is anchored to sleeve 1320 in response to expansion of the hydrogel. Lock tabs 1334 engage hydrogel retention element 1330 as the retention element expands to anchor hydrogel retention element 1330 to sleeve 1320 in response to expansion of the hydrogel retention element.

Figure 14A:
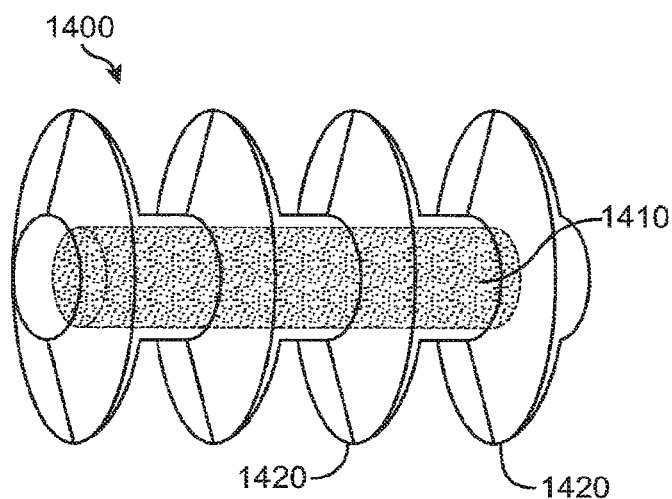
FIG. 14A shows a punctal plug with a drug core and retention fins, according to embodiments of the present invention.

FIG. 14A shows a punctal plug 1400 with a drug core 1410 and retention fins 1420, according to embodiments of the present invention. Retention fins 1420 can comprise a resilient material, for example silicone. Drug core 1410 can comprise many of the drug cores described above and a sheath as described above may be positioned over the drug core to define an exposed area as described above.

Figure 14B:
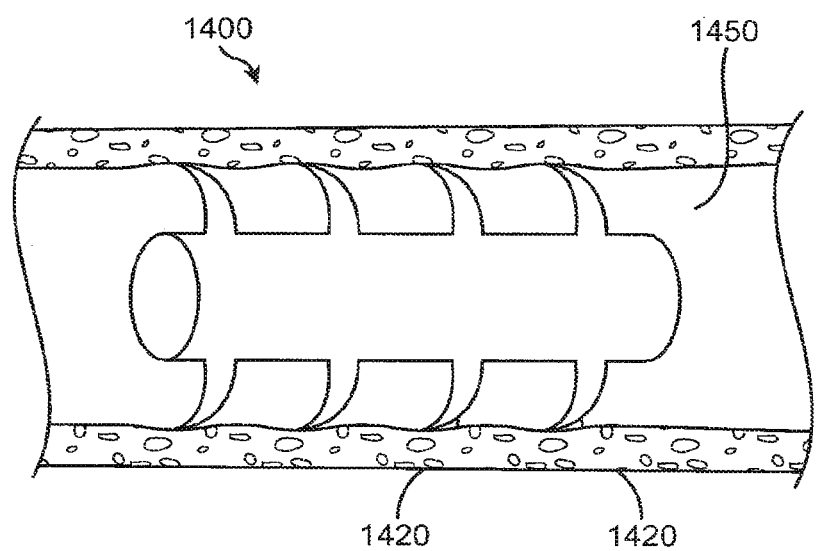
FIG. 14B shows a punctal plug as in 14A the retention fins folded back to retain the plug while the plug is inserted in the canalicular lumen.

FIG. 14B shows punctal plug 1400 as in 14A retention fins 1420 folded back to retain plug 1400 while the plug is inserted in a canalicular lumen 1450. Retention fins 1420 are inclined proximally toward the punctum. This folding back of fins 1420 can wedge the device in the lumen so as to prevent migration. In some embodiments, the plug can comprise a sleeve with wings as described above.

Sheath Body

The sheath body comprises appropriate shapes and materials to control migration of the therapeutic agent from the drug core. The sheath body houses the core and can fit snugly against the core. The sheath body is made from a material that is substantially impermeable to the therapeutic agent so that the rate of migration of the therapeutic agent may be largely controlled by the exposed surface area of the drug core that is not covered by the sheath body. In many embodiments, migration of the therapeutic agent through the sheath body can be about one tenth of the migration of the therapeutic agent through the exposed surface of the drug core, or less, often being one hundredth or less. In other words, the migration of the therapeutic agent through the sheath body is at least about an order of magnitude less that the migration of the therapeutic agent through the exposed surface of the drug core. Suitable sheath body materials include polyimide, polyethylene terephthalate" (hereinafter "PET"). The sheath body has a thickness, as defined from the sheath surface adjacent the core to the opposing sheath surface away from the core, from about 0.00025" to about 0.0015". The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected and/or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the retention structure and sheath body remain implanted in the patient. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body and/or retention structure may have a distinguishing feature, for example a distinguishing color, to show placement such that the placement of the sheath body and/or retention structure in the canaliculus or other body tissue structure can be readily detected by the patient. The retention element and/or sheath body may comprise at least one mark to indicate the depth of placement in the canaliculus such that the retention element and/or sheath body can be positioned to a desired depth in the canaliculus based on the at least one mark.

Retention Structure

The retention structure comprises an appropriate material that is sized and shaped so that the implant can be easily positioned in the desired tissue location, for example the canaliculus. The retention structure is mechanically deployable and typically expands to a desired cross sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments shapeable polymers and coated fibers available from Biogeneral, Inc. of San Diego, California may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the sheath body and drug core are attached to one end of the retention structure as described above, in many embodiments the other end of retention structure is not attached to drug core and sheath body so that the retention structure can slide over the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A protrusion, for example a hook, a loop, or a ring, can extend from the retention structure to facilitate removal of the retention structure.

In many embodiments the sheath and retention structure can comprise two parts.

Occlusive Element

The occlusive element comprises an appropriate material that is sized and shaped so that the implant can at least partially inhibit, even block, the flow of fluid through the hollow tissue structure, for example lacrimal fluid through the canaliculus. The occlusive material shown is a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Therapeutic Agents

A "therapeutic agent" can comprise a drug may be any of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre and post surgical treatments, dry eye and allergies. In some embodiments, the therapeutic agent may be a lubricant or a surfactant, for example a lubricant to treat dry eye.

Exemplary therapeutic agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflaTnmatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Such anti inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, —estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as Bimatoprost, travoprost, Latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

The amount of drug associated with the drug-delivery device may vary depending on the particular agent, the desired therapeutic benefit and the time during which the device is intended to deliver the therapy. Since the devices of the present invention present a variety of shapes, sizes and delivery mechanisms, the amount of drug associated with the device will depend on the particular disease or condition to be treated, and the dosage and duration that is desired to achieve the therapeutic effect. Generally, the amount of drug is at least the amount of drug that upon release from the device, is effective to achieve the desired physiological or pharmacological local or systemic effects.

Embodiments of the drug delivery devices of the present invention can be adapted to provide delivery of drug at a daily rate that is substantially below the therapeutically effective drop form of treatment so as to provide a large therapeutic range with a wide safety margin. For example, many embodiments treat the eye with therapeutic levels for extended periods that are no more than 5 or 10 percent of the daily drop dosage. Consequently, during an initial bolus or washout period of about one to three days, the implant can elute the therapeutic agent at a rate that is substantially higher than the sustained release levels and well below the daily drop form dosage. For example, with an average sustained release level of 100 ng per day, and an initial release rate of 1000 to 1500 ng per day, the amount of drug initially released is less than the 2500 ng of drug that may be present in a drop of drug delivered to the eye. This used use of sustained release levels substantially below the amount of drug in a drop and/or drops administered daily allows the device to release a therapeutically beneficial amount of drug to achieve the desired therapeutic benefit with a wide safety margin, while avoiding an inadequate or excessive amount of drug at the intended site or region.

An extended period of time may mean a relatively short period of time, for example minutes or hours (such as with the use of an anesthetic), through days or weeks (such as the use of pre-surgical or post-surgical antibiotics, steroids, or NSAIDs and the like), or longer (such as in the case of glaucoma treatments), for example months or years (on a recurring basis of use of the device).

For example, a drug such as Timolol maleate, a beta1 and beta2 (non-selective) adrenergic receptor blocking agent can be used in the device for a release over an extended period of time such as 3 months. Three months is a relatively typical elapsed time between physician visits for a glaucoma patient undergoing topical drop therapy with a glaucoma drug, although the device could provide treatment for longer or shorter durations. In the three month example, a 0.25% concentration of Timolol translates to from 2.5 to 5 mg/1000 µL, typically being 2.5 mg/1000 µL. A drop of Timolol for topical application is usually in the range of 40-60 µL, typically being 50 µL. Thus, there may be 0.08-0.15 mg, typically being 0.125 mg of Timolol in a drop. There may be approximately 8% (optionally 6-10%) of the drop left in the eye after 5 minutes, so about 10 µg of the drug is available at that time. Timolol may have a bioavailability of 30-50%, which means that from 1.5 to 7.5 µg, for example 4 µg of the drug is available to the eye. Timolol is generally applied twice a day, so 8 (or 3-15) µg is available to the eye each day. Therefore, a delivery device might contain from 270 to 1350 µg, for example 720 µg, of the drug for a 90 day, or 3 month, extended release. The drug would be contained within the device and eluted based on the polymer or drug/hydrogel concentration. The drug can be similarly contained on the device and eluted for olopatadine hydrochloride (Patanol®) and other drugs in a manner similar to Timolol.

Commercially available solutions of Timolol maleate are available in 0.25% and 0.5% preparations, and the initial dosage can be 1 drop twice per day of 0.25% solution. A 0.25% concentration of Timolol is equivalent to 2.5 mg per 1000 µl. A sustained release quantity of Timolol released each day from the drug core can be from about 3 to 15 ug each day. Although the sustained release quantity delivered each day from the device may vary, a sustained release delivery of about 8 µg per day corresponds to about 3.2% of the 0.250 mg of Timolol applied with two drops of a 0.25% solution.

For example, in the case of Latanoprost (Xalatan), a prostaglandin F2α analogue, this glaucoma medication has concentrations that are about $\frac{1}{10}^{th}$ that of Timolol. Therefore, the amount of drug on the implantable device, depending on the bioavailability, would be significantly less—approximately 20-135 µg and typically 50-100 µg—for Latanoprost and other prostaglandin analogues. This also translates to a device that can either be smaller than one required for a beta blocker delivery or can house more drug for a longer release period.

A drop of Xalatan contains about 2.5 µg of Latanoprost, assuming a 50 µL drop volume. Therefore, assuming that about 8% of 2.5 µg is present 5 minutes after instillation, only about 200 ng of drug remains on the eye. Based on the Latanoprost clinical trials, this amount is effective in lowering IOP for at least 24 hours. Pfizer/Pharmacia conducted several dose-response studies in support of the NDA for Xalatan. The doses ranged from 12.5 µg/mL to 115 µg/mL of Latanoprost. The current dose of Latanoprost, 50 µg/mL, given once per day, was shown to be optimal. However, even the lowest doses of 12.5 µg/mL QD or 15 µg/mL BID consistently gave about 60-75% of the IOP reduction of the 50 µg/mL QD dose. Based on the assumptions above, a 12.5-µg/mL concentration provides 0.625 µg of Latanoprost in a 50 µL drop, which results in only about 50 ng (8%) of drug remaining in the eye after 5 minutes.

In many embodiments, the concentrations of Latanoprost are about $\frac{1}{100}^{th}$, or 1 percent, that of Timolol, and in specific embodiments the concentrations of Latanoprost may be about $\frac{1}{50}^{th}$, or 2 percent, that of Timolol. For example, commercially available solution preparations of Latanoprost are available at concentrations 0.005%, often delivered with one drop per day. In many embodiments, the therapeutically effective concentration of drug released from the device per day can be about $\frac{1}{100}$th of Timolol, about 30 to 150 ng per day, for example about 80 ng, assuming tear washout and bioavailability similar to Timolol. For example, the amount of drug on the implantable device, can be significantly less—approximately 1% to 2% of Timolol, for example 2.7 to 13.5 µg, and can also be about 3 to 20 µg, for Latanoprost and other prostaglandin analogues. Although the sustained release amount of Latanoprost released each day can vary, a sustained release of 80 ng per day corresponds to about 3.2% of the 2.5 µg of Latanoprost applied with a single drop of a 0.005% solution For example, in the case of Bimatoprost (Lumigan), a synthetic prostamide prostaglandin analogue, this glaucoma medication may have concentrations that are $\frac{1}{20}^{th}$ or less than that of Timolol. Therefore, the amount of drug loaded on the extended release device for a 3 to 6 month extended release, depending on the bioavailability, can be significantly less, approximately 5-30 µg and typically 10-20 µg—for Bimatoprost and analogues and derivatives thereof. In many embodiments, the implant can house more drug for a longer sustained release period, for example 20-40 µg for a sustained release period of 6 to 12 months with Bimatoprost and its derivatives. This decrease in drug concentration can also translate to a device that can be smaller than one required for a beta blocker delivery.

Commercially available solution concentrations of Bimatoprost are 0.03% by weight, often delivered once per day. Although the sustained release amount of Bimatnoprost released each day can vary, a sustained release of 300 µg per day corresponds to about 2% of the 15 µg of Bimatoprost applied with a single drop of a 0.03% solution. Work in relation with the present invention suggests that even lower sustained release doses of Bimatoprost can provide at least some reduction in intraocular pressure, for example 20 to 200 ng of Bimatoprost and daily sustained release dosages of 0.2 to 2% of the daily drop dosage.

For example, in the case of Travoprost (Travatan), a prostaglandin F2α analogue, this glaucoma medication may have concentrations that are 2% or less than that of Timolol. For example, commercially available solution concentrations are 0.004%, often delivered once per day. In many embodiments, the therapeutically effective concentration of drug released from the device per day can be about 65 ng, assuming tear washout and bioavailability similar to Timolol. Therefore, the amount of drug on the implantable device, depending on the bioavailability, would be significantly less. This also translates to a device that can either be smaller than one required for a beta blocker delivery or can house more drug for a longer release period. For example, the amount of drug on the implantable device, can be significantly less—approximately $\frac{1}{100}$ of Timolol, for example 2.7 to 13.5 µg, and typically about 3 to 20 µg, for Travoprost, Latanoprost and other prostaglandin F2α analogues. Although the sustained release amount of Latanoprost released each day can vary, a sustained release of 65 ng per day corresponds to about 3.2% of the 2.0 µg of Travoprost applied with a single drop of a 0.004% solution.

In some embodiments, the therapeutic agent may comprise a cortico steriod, for example fluocinolone acetonide, to treat a target ocular tissue. In specific embodiments, fluocinolone acetonide can be released from the canaliculus and delivered to the retina as a treatment for diabetic macular edema (DME).

It is also within the scope of this invention to modify or adapt the devices to deliver a high release rate, a low release rate, a bolus release, a burst release, or combinations thereof. A bolus of the drug may be released by the formation of an erodable polymer cap that is immediately dissolved in the tear or tear film. As the polymer cap comes in contact with the tear or tear film, the solubility properties of the polymer enable the cap to erode and the drug is released all at once. A burst release of a drug can be performed using a polymer that also erodes in the tear or tear film based on the polymer solubility. In this example, the drug and polymer may be stratified along the length of the device so that as the outer polymer layer dissolves, the drug is immediately released. A high or low release rate of the drug could be accomplished by changing the solubility of the erodable polymer layer so that the drug layer released quickly or slowly. Other methods to release the drug could be achieved through porous membranes, soluble gels (such as those in typical ophthalmic solutions), microparticle encapsulations of the drug, or nanoparticle encapsulation, depending on the size of the drug molecule.

Drug Core

The drug core comprises the therapeutic agent and materials to provide sustained release of the therapeutic agent. The therapeutic agent migrates from the drug core to the target tissue, for example ciliary muscles of the eye. The therapeutic agent may optionally be only slightly soluble in the matrix so that a small amount of therapeutic agent is dissolved in the matrix and available for release from the surface of drug core 110. As the therapeutic agent diffuses from the exposed surface of the core to the tear or tear film, the rate of migration from the core to the tear or tear film can be related to the concentration of therapeutic agent dissolved in the matrix. In addition or in combination, the rate of migration of therapeutic agent from the core to the tear or tear film can be related to properties of the matrix in which the therapeutic agent dissolves. In specific embodiments, the rate of migration from the drug core to the tear or tear film can be based on a silicone formulation. In some embodiments, the concentration of therapeutic agent dissolved in the drug core may be controlled to provide the desired rate of release of the therapeutic agent. The therapeutic agent included in the core can include liquid, solid, solid gel, solid crystalline, solid amorphous, solid particulate, and/or dissolved forms of the therapeutic agent. In a preferred embodiment, the drug core comprises a silicone matrix containing the therapeutic agent. The therapeutic agent may comprise liquid or solid inclusions, for example liquid Latanoprost droplets or solid Bimatoprost particles, respectively, dispersed in the silicone matrix.

The drug core can comprise one or more biocompatible materials capable of providing a sustained release of the therapeutic agent. Although the drug core is described above with respect to an embodiment comprising a matrix with a substantially non-biodegradable silicone matrix with inclusions of the drug located therein that dissolve, the drug core can include structures that provide sustained release of the therapeutic agent, for example a biodegradable matrix, a porous drug core, liquid drug cores and solid drug cores. A matrix that contains the therapeutic agent can be formed from either biodegradable or non-biodegradable polymers. A non-biodegradable drug core can include silicone, acrylates, polyethylenes, polyurethane, polyurethane, hydrogel, polyester (e.g., DACRON® from E. I. Du Pont de Nemours and Company, Wilmington, DE), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, IL; CONICHROME® from Carpenter Metals Corp., Wyomissing, PA). A biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly (amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some embodiments the drug core can comprise at least one of hydrogel polymer.

Release of Therapeutic Agent at Effective Levels

The rate of release of the therapeutic agent can be related to the concentration of therapeutic agent dissolved in the drug core. In many embodiments, the drug core comprises non-therapeutic agents that are selected to provide a desired solubility of the therapeutic agent in the drug core. The non-therapeutic agent of the drug core can comprise polymers as described herein and additives. A polymer of the core can be selected to provide the desired solubility of the therapeutic agent in the matrix. For example, the core can comprise hydrogel that may promote solubility of hydrophilic treatment agent. In some embodiments, functional groups can be added to the polymer to provide the desired solubility of the therapeutic agent in the matrix. For example, functional groups can be attached to silicone polymer.

In some embodiments, additives may be used to control the release kinetics of therapeutic agent. For example, the additives may be used to control the concentration of therapeutic agent by increasing or decreasing solubility of the therapeutic agent in the drug core so as to control the release kinetics of the therapeutic agent. The solubility may be controlled by providing appropriate molecules and/or substances that increase and/or decrease the solubility of the dissolved from of the therapeutic agent to the matrix. The solubility of the dissolved from the therapeutic agent may be related to the hydrophobic and/or hydrophilic properties of the matrix and therapeutic agent. For example, surfactants, tinuvin, salts and water can be added to the matrix and may increase the solubility of hydrophilic therapeutic agent in the matrix. In addition, oils and hydrophobic molecules and can be added to the matrix and may increase the solubility of hydrophobic treatment agent in the matrix.

Instead of or in addition to controlling the rate of migration based on the concentration of therapeutic agent dissolved in the matrix, the surface area of the drug core can also be controlled to attain the desired rate of drug migration from the core to the target site. For example, a larger exposed surface area of the core will increase the rate of migration of the treatment agent from the drug core to the target site, and a smaller exposed surface area of the drug core will decrease the rate of migration of the therapeutic agent from the drug core to the target site. The exposed surface area of the drug core can be increased in any number of ways, for example by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. Hydrogels may also be used, and can swell in size to provide a larger exposed surface area. Such hydrogels can also be made porous to further increase the rate of migration of the therapeutic agent.

Further, an implant may be used that includes the ability to release two or more drugs in combination, such as the structure disclosed in U.S. Pat. No. 4,281,654 (Shell). For example, in the case of glaucoma treatment, it may be desirable to treat a patient with multiple prostaglandins or a prostaglandin and a cholinergic agent or an adrenergic antagonist (beta blocker), such as Alphagan®, or a prostaglandin and a carbonic anhydrase inhibitor.

In addition, drug impregnated meshes may be used such as those disclosed in US Patent Publication No. 2002/0055701 or layering of biostable polymers as described in US Patent Publication No. 2005/0129731. Certain polymer processes may be used to incorporate drug into the devices of the present invention such as, so-called "self-delivering drugs" or PolymerDrugs (Polymerix Corporation, Piscataway, NJ) are designed to degrade only into therapeutically useful compounds and physiologically inert linker molecules, further detailed in US Patent Publication No. 2005/0048121 (East), hereby incorporated by reference in its entirety. Such delivery polymers may be employed in the devices of the present invention to provide a release rate that is equal to the rate of polymer erosion and degradation and is constant throughout the course of therapy. Such delivery polymers may be used as device coatings or in the form of microspheres for a drug depot injectable (such as a reservoir of the present invention). A further polymer delivery technology may also be adapted to the devices of the present invention such as that described in US Patent Publication No. 2004/0170685 (Carpenter), and technologies available from Medivas (San Diego, CA).

In specific embodiments, the drug core matrix comprises a solid material, for example silicone, that encapsulates inclusions of the drug. The drug comprises molecules which are very insoluble in water and slightly soluble in the encapsulating drug core matrix. The inclusions encapsulated by the drug core can be micro-particles having dimensions from about 1 µm to about 100 µm across. The drug inclusions can comprise crystals, for example Bimatoprost crystals, and/or droplets of oil, for example with Latanoprost oil. The drug inclusions can dissolve into the solid drug core matrix and substantially saturate the drug core matrix with the drug, for example dissolution of Latanoprost oil into the solid drug core matrix. The drug dissolved in the drug core matrix is transported, often by diffusion, from the exposed surface of the drug core into the tear film. As the drug core is substantially saturated with the drug, in many embodiments the rate limiting step of drug delivery is transport of the drug from the surface of the drug core matrix exposed to the tear film. As the drug core matrix is substantially saturated with the drug, gradients in drug concentration within the matrix are minimal and do not contribute significantly to the rate of drug delivery. As surface area of the drug core exposed to the tear film is nearly constant, the rate of drug transport from the drug core into the tear film can be substantially constant. Work in relation with the present invention suggests that the solubility of the therapeutic agent in water and molecular weight of the drug can effect transport of the drug from the solid matrix to the tear. In many embodiments, the therapeutic agent is nearly insoluble in water and has a solubility in water of about 0.03% to 0.002% by weight and a molecular weight from about 400 grams/mol. to about 1200 grams/mol.

In many embodiments the therapeutic agent has a very low solubility in water, for example from about 0.03% by weight to about 0.002% by weight, a molecular weight from about 400 grams per mole (g/mol.) to about 1200 g/mol, and is readily soluble in an organic solvent. Cyclosporin A (CsA) is a solid with an aqueous solubility of 27.67 µg/mL at 25° C., or about 0.0027% by weight, and a molecular weight (M.W.) of 1202.6 g/mol. Latanoprost (Xalatan) is a prostaglandin F2α analogue, a liquid oil at room temperature, and has an aqueous solubility of 50 µg/mL in water at 25° C., or about 0.005% by weight and a M.W. of 432.6 g/mol. Bimatoprost (Lumigan) is a synthetic prostamide analogue, a solid at room temperature solubility in water of 300 µg/mL in water at 25° C., or 0.03% by weight, and has a M.W. of 415.6 g/mol.

Work in relation with the present invention indicates that naturally occurring surfactants in the tear film, for example surfactant D and phospholipids, may effect transport of the drug dissolved in the solid matrix from the core to the tear film. The drug core can be adapted in response to the surfactant in the tear film to provide sustained delivery of the drug into the tear film at therapeutic levels. For example, empirical data can be generated from a patient population, for example 10 patients whose tears are collected and analyzed for surfactant content. Elution profiles in the collected tears for a drug that is sparingly soluble in water, for example cyclosporine, can also be measured and compared with elution profiles in buffer and surfactant such that an in vitro model of tear surfactant is developed. An in vitro solution with surfactant based on this empirical data can be used to adjust the drug core in response to the surfactant of the tear film.

The drug cores may also be modified to utilize carrier vehicles such as nanoparticles or microparticles depending on the size of the molecule to be delivered such as latent-reactive nanofiber compositions for composites and nano-textured surfaces (Innovative Surface Technologies, LLC, St. Paul, MN), nanostructured porous silicon, known as BiuSilicon®, including micron sized particles, membranes, woven fivers or micromachined implant devices (pSividia, Limited, UK) and protein nanocage systems that target selective cells to deliver a drug (Chimeracore).

In many embodiments, the drug insert comprises of a thin-walled polyimide tube sheath with a drug core comprising Latanoprost dispersed in Nusil 6385 (MAF 970), a medical grade solid silicone that serves as the matrix for drug delivery. The distal end of the drug insert is sealed with a cured film of solid Loctite 4305 medical grade adhesive. The drug insert may be placed within the bore of the punctum plug, the Loctite 4305 adhesive does not come into contact with either tissue or the tear film. The inner diameter of the drug insert can be 0.32 mm; and the length can be 0.95 mm. Three Latanoprost concentrations in the finished drug product can be tested clinically: Drug cores can comprise 3.5, 7 or 14 µg Latanoprost, with percent by weight concentrations of 5, 10 and 20 respectively. Assuming an overall elution rate of approximately 100 ng/day, the drug core comprising 14 µg of Latanoprost is adapted to deliver drug for approximately at least 100 days, for example 120 days. The overall weight of the drug core, including Latanoprost, can be ~70 µg. The weight of the drug insert including the polyimide sleeve can be approximately 100 µg.

In many embodiments, the drug core may elute with an initial elevated level of therapeutic agent followed by substantially constant elution of the therapeutic agent. In many instances, an amount of therapeutic agent released daily from the core may be below the therapeutic levels and still provide a benefit to the patient. An elevated level of eluted therapeutic agent can result in a residual amount of therapeutic agent and/or residual effect of the therapeutic agent that is combined with a sub-therapeutic amount of therapeutic agent to provide relief to the patient. In embodiments where therapeutic level is about 80 ng per day, the device may deliver about 100 ng per day for an initial delivery period. The extra 20 ng delivered per day can have a beneficial effect when therapeutic agent is released at levels below the therapeutic level, for example at 60 ng per day. As the amount of drug delivered can be precisely controlled, an initial elevated dose may not result in complications and/or adverse events to the patient.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for delivery of a therapeutic agent to an eye of a patient using a punctal plug, comprising:
   positioning the punctal plug into a lacrimal punctum of an eye wherein the punctal plug comprises a plug body and a drug insert, wherein the drug insert comprises a drug core comprising a therapeutic agent and a polymer matrix, and wherein the plug body comprises silicone; and,
   an impermeable sheath body partially covering the drug core, wherein the sheath body is configured to provide an exposed proximal end of the drug core in direct contact with tear fluid that releases the therapeutic agent to the eye; and,
   delivering a dose of the therapeutic agent to the eye for a sustained treatment period, wherein the punctal plug remains in position for the sustained treatment period for at least of one week to 3 months.

2. The method of claim 1, wherein the therapeutic agent comprises anti-glaucoma medications, antimicrobial agents, a corticosteroid, non-steroidal anti-inflammatories, a decongestant, an antihistamine, a cytokine inhibitor, a leucotriene inhibitor, an IgE inhibitor, an immunomodulator, a mast cell stabilizer, a cycloplegic, a lubricant or a surfactant.

3. The method of claim 1, wherein the therapeutic agent is a corticosteroid.

4. The method of claim 1, wherein the therapeutic agent is selected from a lubricant or a surfactant.

5. The method of claim 1, wherein the therapeutic agent is selected from the group consisting of latanoporost, bimatoprost, timolol maleate, travoprost, cyclosporine and non-steroidal anti-inflammatories.

6. The method of claim 1, wherein the therapeutic agent is cyclosporine.

7. The method of claim 1, wherein the drug core of the punctal plug is further configured to deliver a bolus dose of the therapeutic agent.

8. The method of claim 1, wherein the drug core of the punctal plug is further configured to deliver a burst dose of the therapeutic agent at a beginning of the treatment period.

9. The method of claim 1, wherein the polymeric matrix comprises silicone, acrylate, polyethylene, polyurethane, polyester, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) or combinations thereof.

10. The method of claim 1, wherein the polymer matrix comprises polyurethane, polycaprolactone or polyethylene.

11. The method of claim 1, wherein the drug core further comprises one or more additives to increase or decrease solubility of the therapeutic agent for controlled release of the therapeutic agent.

12. The method of claim 11, wherein the one or more additives is selected from the group consisting of surfactants, tinuvin, salts and water.

13. The method of claim 1, wherein a distal end of the drug core is sealed with a medical grade adhesive.

14. The method of claim 1, wherein delivery of the therapeutic agent comprises pre and/or post-surgical treatments.

\* \* \* \* \*